(12) United States Patent
Clary et al.

(10) Patent No.: US 9,266,848 B2
(45) Date of Patent: *Feb. 23, 2016

(54) 4-ALKOXY-N-(2-HYDROXYCARBAMOYL-2-PIPERIDINYL-ETHYL)-BENZAMIDE COMPOUNDS AS SELECTIVE TACE-INHIBITORS FOR THE TREATMENT OF INFLAMMATORY DISEASES

(75) Inventors: Laurence Clary, La Colle sur Loup (FR); Jean-Claude Pascal, Nice (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 816 days.

This patent is subject to a terminal disclaimer.

(21) Appl. No.: 13/496,577

(22) PCT Filed: Sep. 16, 2010

(86) PCT No.: PCT/EP2010/063595
§ 371 (c)(1),
(2), (4) Date: May 24, 2012

(87) PCT Pub. No.: WO2011/033010
PCT Pub. Date: Mar. 24, 2011

(65) Prior Publication Data
US 2012/0226033 A1  Sep. 6, 2012

(30) Foreign Application Priority Data
Sep. 17, 2009 (FR) ..................... 09 56377

(51) Int. Cl.
| | |
|---|---|
| C07D 295/15 | (2006.01) |
| C07D 213/30 | (2006.01) |
| C07D 213/61 | (2006.01) |
| C07D 215/14 | (2006.01) |
| C07D 267/22 | (2006.01) |
| C07D 401/12 | (2006.01) |
| C07D 403/12 | (2006.01) |
| C07D 471/04 | (2006.01) |

(52) U.S. Cl.
CPC ............ *C07D 295/15* (2013.01); *C07D 213/30* (2013.01); *C07D 213/61* (2013.01); *C07D 215/14* (2013.01); *C07D 267/22* (2013.01); *C07D 401/12* (2013.01); *C07D 403/12* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 8,772,478 B2* | 7/2014 | Clary et al. | ............ 544/62 |
| 8,852,863 B2 | 10/2014 | Rothmann et al. | |
| 2004/0072802 A1 | 4/2004 | Duan et al. | |
| 2012/0116072 A1* | 5/2012 | Clary et al. | .......... 540/481 |

FOREIGN PATENT DOCUMENTS

| | | |
|---|---|---|
| JP | 2003-519211 A | 6/2003 |
| JP | 2012-529266 A | 11/2012 |
| WO | 01/49657 A1 | 7/2001 |
| WO | WO-02/30873 A1 | 4/2002 |
| WO | WO-2004/062601 A2 | 7/2004 |
| WO | 2008/045671 A1 | 4/2008 |

OTHER PUBLICATIONS

Patani. Chemical Reviews, 1996, 96, 3147-76.*
Yokota et al., "MMP/ADAM inhibitors: Therapeutic potential for psoriasis", Expert Opinion on Therapeutic Patents, vol. 15, No. 4, Jan. 1, 2005, pp. 421-435.
Le et al., "Inhibitors of Tace and Caspase-1 as Anti-inflammatory Drugs", Current Medicinal Chemistry, vol. 12, No. 25, Jan. 1, 2005, pp. 2963-2977.
International Preliminary Report on Patentability and Written Opinion of the International Searching Authority issued Mar. 20, 2012 in corresponding Appln No. PCT/EP2010/063595.

* cited by examiner

*Primary Examiner* — Noble Jarrell
(74) *Attorney, Agent, or Firm* — Dentons US LLP

(57) ABSTRACT

The present invention relates to novel benzene-carboxamide compounds having a structure that corresponds to the general formula (I) below: and also to their method of synthesis and to their use in pharmaceutical compositions intended for use in human or veterinary medicine or else to their use in cosmetic compositions.

(I)

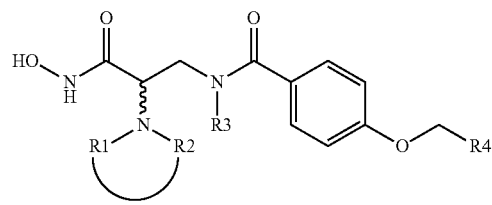

20 Claims, 2 Drawing Sheets

4-ALKOXY-N-(2-HYDROXYCARBAMOYL-2-PIPERIDINYL-ETHYL)-BENZAMIDE COMPOUNDS AS SELECTIVE TACE-INHIBITORS FOR THE TREATMENT OF INFLAMMATORY DISEASES

CROSS REFERENCE TO RELATED APPLICATIONS

This application is a National Phase filing under 35 U.S.C. §371 of PCT/EP2010/063595 filed on Sep. 16, 2010; and this application claims priority to Application No. 0956377 filed in France on Sep. 17, 2009 under 35 U.S.C. §119; and claims the benefit of U.S. Provisional Application No. 61/272,368 filed Sep. 17, 2009. The entire contents of each of these applications are hereby incorporated by reference.

TECHNICAL FIELD

The present invention relates to novel benzene-carboxamide compounds corresponding to the general formula (I) below:

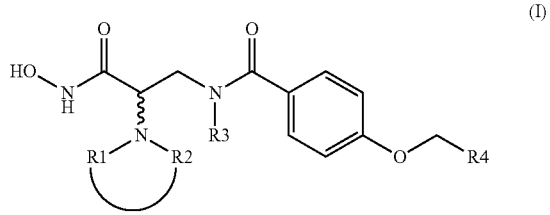

and also to their method of synthesis and to their use in pharmaceutical compositions intended for use in human or veterinary medicine.

The compounds of the present invention act as inhibitors of the TNFα-converting enzyme, also known as TACE. Therefore, they are of use in the treatment of diseases for which reducing the production of TNFα is of great benefit.

The present invention also relates to the use of compounds corresponding to the general formula (I) in cosmetic compositions.

PRIOR ART

Adamalysins ("ADAMs" or A Disintegrin and Metalloproteinase) are a sub-family of zinc metalloendopeptidase enzymes. Their ectodomain comprises a protease domain, the activation of which depends on the zinc, a disintegrin domain and a cysteine-rich domain. To date, at least 30 different ADAMs have been identified, the first one of which to be characterized was ADAM17, also known as TACE (TNFα-converting enzyme) [Gueydan C et al. Med. Sci 1997, 13, 83-88; Black R. A et al. Nature 1997, 385:729-733; Moss et al. Nature 1997, 385:733-736]. TACE mRNA is present in numerous tissues and more particularly in monocytes, macrophages, T lymphocytes but also in keratinocytes for example.

TACE is responsible for the cleavage of pro-TNFα, a 26 kDa membrane protein, in order to result in the release of soluble TNFα, a biologically active 17 kDa protein [Schlondorff et al. Biochem. J. 2000, 347, 131-138]. The soluble TNFα released by the cell is capable of acting on sites very far from the site of synthesis. TNFα is involved in a large number of pro-inflammatory biological processes [Aggarwal et al, Eur. Cytokine Netw., 1996, 7: 93-124]. Several pharmacological and clinical studies have clearly shown that blocking the effects of TNFα with specific antibodies or anti-TNFα biological agents (Etanercept, Adalimumab, Infliximab) was beneficial in the treatment of autoimmune diseases such as rheumatoid arthritis [Feldman et al., Lancet, 1994, 344, 1105), non-insulin-dependent diabetes mellitus [Lohmander L. S. et al., Arthritis Rheum, 1993, 36, 1214-1222], and Crohn's disease [MacDonald et al., Clin. Exp. Immunol. 1990, 81, 301].

TNFα also plays a fundamental role during the inflammatory phenomenon triggered in psoriasis lesions. The serum TNFα levels are high in psoriatic patients [Mussi A et al. J. Biol. Regul. Homeost Agents, 1997, 11, 115-118]; the TNFα levels are also high in the actual psoriatic plaques [Bonifati C. et al. Clin. Exp. Dermatol., 1994, 19, 383-387]. The key cells in the physiopathology of psoriasis are the keratinocytes, the dendritic cells and certain T lymphocytes. The interaction between these families of cells results in an inflammatory cascade leading to the lesions characteristic of psoriasis with release of TNFα [Kupper T S, N. Engl. J. Med, 2003, 349, 1987-1990]. Clinical studies for the treatment of moderate to severe plaque psoriasis by anti-TNFα biological agents (Etanercept, Adalimumab, Infliximab) demonstrated their effectiveness both on psoriatic lesions and on the quality of life of the patients [Ortonne J P, Annales de dermatologie et de vénéreologie, 2005, 132 (8-9 pt2), 4S6-9 and 2005, 132, 9S01-9S70].

Thus, compounds which inhibit the production of TNFα are of great benefit for the treatment of inflammatory diseases and diseases involving release of TNFα.

SUMMARY OF THE INVENTION

Our invention therefore describes novel molecules which inhibit the TACE enzyme (TNFα-converting enzyme) and therefore inhibit the secretion of soluble TNFα (active form of TNFα) by cells. These novel molecules are therefore potential active principles for the treatment of pathologies that involve a reduction or an inhibition of TNFα production. By way of illustration, and non-limitingly, these pathologies are, for example, septic shock, haemodynamic shock, malaria, inflammatory bowel diseases (IBDs) such as Crohn's disease and ulcerative colitis, inflammatory bone diseases, mycobacterium infections, meningitis, fibrotic diseases, heart diseases, ischaemic attack, graft rejection, cancer, atherosclerosis, obesity, diseases involving angiogenesis phenomena, autoimmune diseases, osteoarthritis, rheumatoid arthritis, ankylosing spondylitis, chronic juvenile arthritis, multiple sclerosis, HIV, non-insulin-dependent diabetes mellitus, allergic diseases, asthma, chronic obstructive pulmonary disease (COPD), ocular inflammation, inflammatory diseases of the skin, psoriasis, atopic dermatitis and psoriatic arthritis.

These molecules are also potential active principles for the treatment of neurological pathologies having an inflammatory nature, for which reducing the production of TNFα would be of great benefit. These pathologies listed below in a non-limiting manner are, for example, Alzheimer's disease, Parkinson's disease, Parkinsonian disorders, amyotrophic lateral sclerosis, autoimmune diseases of the nervous system, autonomic diseases of the nervous system, dorsal pains, cerebral oedema, cerebrovascular diseases, dementia, nerve fibre demyelinating autoimmune diseases of the nervous system, diabetic neuropathies, encephalitis, encephalomyelitis, epilepsy, chronic fatigue syndrome, giant cell arteritis, Guillain-Barré syndrome, headaches, multiple sclerosis, neuralgia, peripheral nervous system diseases, polyneuropathies, polyradiculoneuropathy, radiculopathy, respiratory paralyses, spinal cord diseases, Tourette syndrome, central nervous system vasculitis, Huntington's disease and cerebral attack.

A large variety of TACE inhibitors are already known as indicated below. However, a large number of these inhibitors do not act selectively on the TACE enzyme relative to other enzymes from the family of ADAMs and/or matrix metalloproteinases (MMPs).

However, the non-selective inhibition of these families of enzymes induces undesirable side effects observed in vivo. For example, the inhibition of MMP-1 (collagenase-1) has been associated with musculoskeletal toxicity problems.

As a non-selective inhibitor, mention may also be made of Apratastat, a known inhibitor tested in phase 2 clinical trials for the treatment of rheumatoid arthritis (Curr Opin Investig Drugs. 2006 November; 7 (11), 1014-9). This inhibitor is not selective for the TACE enzyme compared to certain MMPs (WO 00/44709; page 251, table 10, example 61).

Certain cyclic β-amido hydroxamic derivatives have already been described in WO 99/37625, WO 00/044730, WO 03/055856 and EP 01/301989 as matrix metalloproteinase inhibitors and/or TACE inhibitors. Other patents (WO 98/15525, WO 00/059874, WO 02/030873) claim non-cyclic amide derivatives as inhibitors of matrix metalloproteinases and/or of TNFα and/or of aggrecanase. Other non-cyclic β-amido hydroxamic derivatives are described as antibacterial agents in patents WO 04/062601 and WO 08/154642. Patent WO 01/070734 claims, in a very broad general structure, β-amino acid derivatives as inhibitors of matrix metalloproteases and of TNFα, without presenting biological results on the TACE enzyme.

However, the applicant has now discovered, unexpectedly and surprisingly, that novel compounds of general formula (I) have a very good TACE-inhibiting activity and in particular inhibit the TACE enzyme very selectively relative to other ADAMs and MMPs.

Thus, the present invention relates to compounds of general formula (I) below:

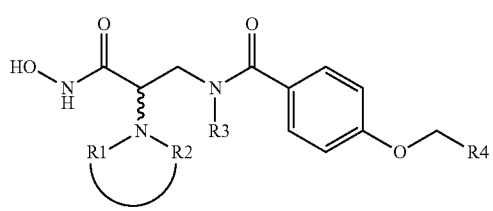

(I)

in which:

$R_1$ and $R_2$ are identical or different and represent alkyl radicals or else they form a ring with the nitrogen atom to which they are attached, said ring being represented by the following formula:

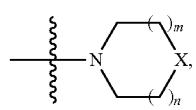

X, m and n having the meanings given below;
$R_3$ is a hydrogen atom or a lower alkyl radical;
$R_4$ is an alkyl radical, a substituted alkyl radical, an alkenyl radical, a substituted alkenyl radical, an alkynyl radical, a substituted alkynyl radical, an aryl radical, a substituted aryl radical, an aralkyl radical, a substituted aralkyl radical, a heterocyclic radical, a substituted heterocyclic radical, a cycloalkyl radical, a substituted cycloalkyl radical, a heteroaryl radical, a substituted heteroaryl radical, a heteroaralkyl radical or a substituted heteroaralkyl radical;

X represents an oxygen atom, a —$CH_2$— radical, a —CH—($CH_2$)$_p$—$NR_5R_6$ radical, a sulphur atom, an SO radical or an $SO_2$ radical, $R_5$, $R_6$ and p having the meanings given below;

$R_5$ and $R_6$, which may be identical or different, represent a hydrogen atom, an alkyl radical, a substituted alkyl radical, an aryl radical or a substituted aryl radical;

m may take the values of 0 or 1;
n may take the values of 0, 1, 2 or 3;
p may take the values of 0, 1 or 2;

and also the addition salts of the compounds of general formula (I) with a pharmaceutically acceptable acid, the addition salts of the compounds of general formula (I) with a pharmaceutically acceptable base and the enantiomers of the compounds of general formula (I).

Among the addition salts of the compounds of general formula (I) with a pharmaceutically acceptable acid, mention may preferably be made of the salts with an organic acid or with an inorganic acid.

Suitable inorganic acids are, for example, hydrohalic acids such as hydrochloric acid and hydrobromic acid, sulphuric acid, nitric acid and phosphoric acid.

Suitable organic acids are, for example, acetic acid, trifluoroacetic acid, trichloroacetic acid, propionic acid, glycolic acid, pyruvic acid, succinic acid, benzoic acid, cinnamic acid, mandelic acid, methanesulphonic acid, para-toluenesulphonic acid, salicylic acid, picric acid, citric acid, oxalic acid, tartaric acid, malonic acid, maleic acid, camphor-sulphonic acid and fumaric acid.

Among the addition salts of the compounds of general formula (I) with a pharmaceutically acceptable base, mention may preferably be made of the salts with an organic base or with an inorganic base.

Suitable inorganic bases are the hydroxides of alkali metals or of alkaline-earth metals or carbonates of alkali metals or of alkaline-earth metals. Among these bases, mention may be made, for example, of potassium hydroxide, sodium hydroxide, lithium hydroxide, calcium hydroxide, potassium carbonate, sodium carbonate and calcium carbonate.

Suitable organic bases include amines and amino acids. Among the amines, mention may be made, for example, of aliphatic or aromatic primary, secondary or tertiary amines such as methylamine, ethylamine, ethanolamine, propylamine, isopropylamine, the 4 isomers of butylamine, dimethylamine, diethylamine, diethanolamine, dipropylamine, diisopropylamine, di-n-butylamine, pyrrolidine, piperidine, morpholine, diethanolphenylamine, trimethylamine, triethylamine, tripropylamine, quinuclidine, pyridine, quinoline and isoquinoline.

Among the amino acids, mention may be made, for example, of lysine, arginine and ornithine.

According to the present invention, the expression "lower alkyl radical" denotes a linear or branched saturated hydrocarbon-based chain comprising from 1 to 4 carbon atoms.

According to the present invention, the expression "alkyl radical" denotes a linear or branched saturated hydrocarbon-based chain comprising from 1 to 10 carbon atoms.

According to the present invention, the expression "alkenyl radical" denotes a linear or branched unsaturated hydrocarbon-based chain comprising from 2 to 10 carbon atoms and comprising one or more double bonds.

According to the present invention, the expression "alkynyl radical" denotes a linear or branched unsaturated hydrocarbon-based chain comprising from 2 to 10 carbon atoms and comprising one or more triple bonds.

According to the present invention, the expression "substituted alkyl radical" denotes a linear or branched saturated hydrocarbon-based chain comprising from 1 to 10 carbon atoms and substituted with one or more radicals chosen from a halogen atom, an alkoxy radical and a hydroxyl radical.

According to the present invention, the expression "substituted alkenyl radical" denotes a linear or branched unsaturated hydrocarbon-based chain comprising from 2 to 10 carbon atoms, comprising one or more double bonds and substituted with one or more radicals chosen from a halogen atom, an alkoxy radical and a hydroxyl radical.

According to the present invention, the expression "substituted alkynyl radical" denotes a linear or branched unsaturated hydrocarbon-based chain comprising from 2 to 10 carbon atoms, comprising one or more triple bonds and substituted with one or more radicals chosen from a halogen atom, an alkoxy radical and a hydroxyl radical.

According to the present invention, the term "cycloalkyl" denotes a cyclic saturated hydrocarbon-based chain comprising from 3 to 7 carbon atoms.

According to the present invention, the expression "substituted cycloalkyl" denotes a cyclic saturated hydrocarbon-based chain comprising from 3 to 7 carbon atoms and substituted with one or more radicals chosen from a halogen atom, an alkoxy radical and a hydroxyl radical.

According to the present invention, the expression "aryl radical" denotes an aromatic hydrocarbon-based ring or two fused aromatic hydrocarbon-based rings.
The preferred aryl radicals are chosen from phenyl and naphthyl radicals.

According to the present invention, the expression "substituted aryl radical" denotes an aromatic hydrocarbon-based ring or two fused aromatic hydrocarbon-based rings substituted with one or more groups of atoms chosen from an alkyl, an alkoxy, an aryl, a halogen, a hydroxyl, a cyano, a trifluoromethyl and a nitro.

According to the present invention, the expression "aralkyl radical" denotes an alkyl substituted with an aryl.

According to the present invention, the expression "substituted aralkyl radical" denotes an alkyl substituted with a substituted aryl.

According to the present invention, the expression "heterocyclic radical" denotes a saturated or unsaturated, cyclic or polycyclic hydrocarbon-based chain comprising one or more heteroatoms chosen from O, S and N.

According to the present invention, the expression "substituted heterocyclic radical" denotes a heterocyclic radical substituted with one or more groups of atoms chosen from an alkyl, an alkoxy, a halogen, a hydroxyl, a cyano, a trifluoromethyl and a nitro.

According to the present invention, the expression "heteroaryl radical" denotes an aromatic heterocyclic radical, that is to say an aromatic, cyclic or polycyclic, hydrocarbon-based chain comprising one or more heteroatoms chosen from O, S and N.

According to the present invention, the expression "substituted heteroaryl radical" denotes a heteroaryl radical substituted with one or more groups of atoms chosen, for example, from an alkyl, an alkoxy, an aryl, a substituted aryl, a halogen, a hydroxy, a cyano, a trifluoromethyl and a nitro.

According to the present invention, the expression "heteroaralkyl radical" denotes an alkyl radical substituted with a heteroaryl radical.

According to the present invention, the expression "substituted heteroaralkyl radical" denotes a heteroaralkyl radical substituted with one or more groups of atoms chosen from an alkyl, an alkoxy, a halogen, a hydroxyl, a cyano, a trifluoromethyl and a nitro.

According to the present invention, the expression "alkoxy radical" denotes an oxygen atom substituted with an alkyl radical.

According to the present invention, the expression "halogen atom" denotes a fluorine, chlorine, bromine or iodine atom.

Among the compounds of general formula (I) that fall within the scope of the present invention, mention may especially be made of the following compounds:

1. 4-but-2-ynyloxy-N—((S)-2-hydroxycarbamoyl-2-piperidin-1-ylethyl)benzamide
2. N—((S)-2-hydroxycarbamoyl-2-piperidin-1-ylethyl)-4-(2-methylquinolin-4-ylmethoxy)benzamide
3. N—((S)-2-hydroxycarbamoyl-2-piperidin-1-ylethyl)-4-(2-methylquinolin-4-ylmethoxy)benzamide
4. N—((S)-2-hydroxycarbamoyl-2-piperidin-1-ylethyl)-4-(2-phenylpyridin-4-ylmethoxy)benzamide
5. N—((S)-2-hydroxycarbamoyl-2-piperidin-1-ylethyl)-4-(pyridin-4-ylmethoxy)benzamide
6. 4-(4-cyanobenzyloxy)-N—((S)-2-hydroxycarbamoyl-2-piperidin-1-ylethyl)benzamide
7. N—((S)-2-hydroxycarbamoyl-2-piperidin-1-ylethyl)-4-(4-methylnaphthalen-1-ylmethoxy)benzamide
8. 4-(2-bromopyridin-4-ylmethoxy)-N—((S)-2-hydroxycarbamoyl-2-piperidin-1-ylethyl)benzamide
9. N—((S)-2-hydroxycarbamoyl-2-morpholin-4-ylethyl)-4-(pyridin-4-ylmethoxy)benzamide
10. N—((S)-2-hydroxycarbamoyl-2-morpholin-4-ylethyl)-4-[2-(2-trifluoromethylphenyl)pyridin-4-ylmethoxy]-benzamide
11. N—((S)-2-diethylamino-2-hydroxycarbamoylethyl)-4-(2-methylquinolin-4-ylmethoxy)benzamide
12. N—((S)-2-hydroxycarbamoyl-2-pyrrolidin-1-ylethyl)-4-(2-methylquinolin-4-ylmethoxy)benzamide
13. N—((S)-2-hydroxycarbamoyl-2-pyrrolidin-1-ylethyl)-4-(3-methylbenzyloxy)benzamide
14. N—((R)-2-hydroxycarbamoyl-2-piperidin-1-ylethyl)-4-(2-methylquinolin-4-ylmethoxy)benzamide
15. N—((R)-2-azepan-1-yl-2-hydroxycarbamoylethyl)-4-(2-methylquinolin-4-ylmethoxy)benzamide
16. N—((S)-2-azepan-1-yl-2-hydroxycarbamoylethyl)-4-(2-methylquinolin-4-ylmethoxy)benzamide
17. N—((S)-2-hydroxycarbamoyl-2-[1,4]oxazepan-4-ylethyl)-4-(2-methylpyridin-4-ylmethoxy)benzamide
18. N—((S)-2-hydroxycarbamoyl-2-thiomorpholin-4-ylethyl)-4-(1-methylpiperidin-4-ylmethoxy)benzamide
19. N—((S)-2-hydroxycarbamoyl-2-thiomorpholin-4-ylethyl)-4-(2-methylquinolin-4-ylmethoxy)benzamide
20. N—((S)-2-hydroxycarbamoyl-2-piperidin-1-ylethyl)-4-(pyrazolo[1,5-a]pyridin-3-ylmethoxy)benzamide
21. N—((S)-2-hydroxycarbamoyl-2-morpholin-4-ylethyl)-4-(2-trifluoromethylpyrazolo[1,5-a]pyridin-3-ylmethoxy)-benzamide
22. N—((S)-2-hydroxycarbamoyl-2-piperidin-1-ylethyl)-4-(2-trifluoromethylpyrazolo[1,5-a]pyridin-3-ylmethoxy)-benzamide
23. N—[(S)-2-(1,1-dioxothiomorpholin-4-yl)-2-hydroxycarbamoylethyl]-4-(4-fluorobenzyloxy)benzamide
24. N—((S)-2-hydroxycarbamoyl-2-pyrrolidin-1-ylethyl)-4-(2-methylnaphthalen-1-ylmethoxy)-N-propylbenzamide
25. N—((S)-2-hydroxycarbamoyl-2-pyrrolidin-1-ylethyl)-4-propoxybenzamide 26. N—((S)-2-hydroxycarbamoyl-2-piperidin-1-ylethyl)-4-(quinolin-4-ylmethoxy)benzamide
27. N—((S)-2-azocan-1-yl-2-hydroxycarbamoylethyl)-4-(3-methyl-1H-pyrazol-4-ylmethoxy)benzamide
28. 4-(3,5-dimethylbenzyloxy)-N—((S)-2-hydroxy-carbamoyl-2-[1,4]oxazocan-4-ylethyl)benzamide
29. 4-(2,6-dimethylpyridin-4-ylmethoxy)-N—[(S)-2-(ethylpropylamino)-2-hydroxycarbamoylethyl]benzamide
30. N—((R)-2-azepan-1-yl-2-hydroxycarbamoylethyl)-4-(2-methylpyridin-4-ylmethoxy)benzamide
31. N—[(S)-2-(4-ethylaminopiperidin-1-yl)-2-hydroxy-carbamoylethyl]-4-(2-methylquinolin-4-ylmethoxy)-benzamide
32. N—[(S)-2-(3-aminopyrrolidin-1-yl)-2-hydroxy-carbamoylethyl]-4-(2-methylquinolin-4-ylmethoxy)-benzamide
33. N—[(S)-2-(3-dimethylaminomethylpyrrolidin-1-yl)-2-hydroxycarbamoylethyl]-4-(2-methylquinolin-4-yl-methoxy)benzamide
34. N—[(S)-2-(4-benzylaminopiperidin-1-yl)-2-hydroxycarbamoylethyl]-4-(2-methylpyridin-4-ylmethoxy)-benzamide and
35. N—[(S)-2-(4-dimethylaminomethylazepan-1-yl)-2-hydroxycarbamoylethyl]-4-(2-methyl-1H-indol-3-yl-methoxy)benzamide.

The compounds of general formula (I) in which R1 and R2 form a ring are prepared according to the reaction scheme from FIG. 1 presented below.

According to FIG. 1, the compounds (3) are obtained by a reaction between the amino acid (1) H-DAP(Boc)-OMe.HCl or H-(D)-DAP(Boc)-OMe.HCl and the compound (2) (commercial or previously prepared) in the presence of a tertiary organic base such as diisopropylethylamine or triethylamine at a temperature between 60° C. and 120° C. The compounds (4) are obtained by deprotection of the amine functional group of the compounds (3) according to conventional methods such as, for example, the use of a solution of hydrochloric acid in isopropanol.

A reaction between the compound (4) and the 4-hydroxybenzoyl chloride O-protected by a benzyl group (6) in the presence of a tertiary base such as, for example, triethylamine in dichloromethane leads to the compound (7). N-alkylation of the amide functional group may then be carried out by reaction with an alkyl halide in the presence of a base such as, for example, sodium hydride in a solvent such as DMF in order to lead to the derivative (8). The compound (9) is obtained by deprotection according to methods known to a person skilled in the art for deprotecting a phenol functional group. The compound (10) is obtained by alkylation of the phenol functional group of the compound (9) by reaction with an alkyl halide in the presence of a base such as, for example, caesium carbonate in acetone or by Mitsunobu reaction with a primary alcohol derivative in the presence of triphenylphosphine and diisopropylazodicarboxylate for example. Via a saponification reaction in the presence of a base such as lithium hydroxide in the presence of water and tetrahydrofuran, the compound (11) is obtained. In a last step, the compound (12) is obtained by coupling between the 0-(tert-butyldimethylsilyl) hydroxylamine for example and the derivative (11) under conventional peptide coupling conditions, using, for example, as coupling agents, 1-(3-dimethylaminopropyl)-3-ethylcarbodiimide hydrochloride, hydroxybenzotriazole or TBTU and, as a base, triethylamine or diisopropylethylamine in a solvent such as dichloromethane or dimethylformamide. The deprotection of the silylated hydroxamic acid intermediately formed takes place in situ or by washing with an acid aqueous solution in order to result in the compound (12).

Another alternative for obtaining the compound (12) is presented in FIG. 2 below.

According to the synthesis scheme from FIG. 2, the derivative (3) may optionally be alkylated in the presence of a base such as sodium hydride and of an alkyl halide in dimethylformamide for example to result in the compound (13) from which the compound (14) is obtained according to conventional methods for the deprotection of amines such as, for example, the use of a solution of hydrochloric acid in isopropanol.

Via alkylation of methyl 4-hydroxybenzoate with an $R_4CH_2Br$ derivative for example in the presence of a base such as potassium carbonate, the compound (15) is obtained. After saponification of the compound (15), the derivative (16) obtained is placed in thionyl chloride for example in order to result in the derivative (17).

The derivative (10) is obtained by a reaction between the compounds (14) and (17) in the presence of a base such as triethylamine in dichloromethane for example. The compound (12) is then obtained from the derivative (10) according to the same reaction pathway as that presented in FIG. 1.

The compounds of general formula (I) in which R1 and R2, which are identical or different, are alkyl radicals are prepared according to the reaction scheme of FIG. 3 presented below. According to FIG. 3, the compounds (18) are obtained by a reaction between the amino acid (1) H-DAP(Boc)-OMe.HCl or H-(D)-DAP(Boc)-OMe.HCl and an alkyl halide in the presence of a tertiary organic base such as diisopropylethylamine or triethylamine at a temperature between 60° C. and 120° C. Reductive amination with an aliphatic aldehyde in the presence of sodium cyanoborohydride for example makes it possible to obtain the derivative (19).

After deprotection of the amine functional group, the compound (20) is obtained. It is then condensed with p-alkoxybenzoyl chloride (17) (prepared according to the scheme from FIG. 2) in order to result in the derivative (21). In the case where R3 is a lower alkyl radical, an N-alkylation of the sulphonamide functional group is then carried out by reaction with an alkyl halide in the presence of a base such as, for example, potassium carbonate in a solvent such as DMF in order to result in the derivative (22). Via a saponification reaction in the presence of a base such as lithium hydroxide in the presence of water and tetrahydrofuran for example, the compound (23) is obtained. In a final step, the compound (24) is obtained by coupling between O-(tert-butyldimethylsilyl) hydroxylamine for example and the derivative (23) under conventional peptide coupling conditions, using, for example, as coupling agents, 1-(3-dimethylaminopropyl)-3-ethylcarbodiimide hydrochloride, hydroxybenzotriazole or TBTU and, as a base, triethylamine or diisopropylethylamine in a solvent such as dichloromethane or dimethylformamide. The deprotection of the silylated hydroxamic acid takes place in situ or by washing with a slightly acid aqueous solution in order to result in the compound (24).

According to the present invention, the compounds of general formula (I) that are preferred are those for which:
$R_1$ and $R_2$, which are identical or different, represent alkyl radicals or else they form a ring with the nitrogen atom to which they are attached, said ring being represented by the following formula:

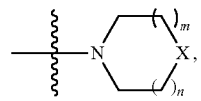

X, m and n having the meanings given below;

$R_3$ is a hydrogen atom or a lower alkyl radical;

$R_4$ is an alkynyl radical, a substituted alkynyl radical, an aryl radical, a substituted aryl radical, an aralkyl radical, a substituted aralkyl radical, a heterocyclic radical, a substituted heterocyclic radical, a heteroaryl radical, a substituted heteroaryl radical, a heteroaralkyl radical or a substituted heteroaralkyl radical;

X represents an oxygen atom, a —$CH_2$— radical, a —CH—($CH_2$)$_p$—$NR_5R_6$ radical, a sulphur atom, an SO radical or an $SO_2$ radical, $R_5$, $R_6$ and p having the meanings given below;

$R_5$ and $R_6$, which may be identical or different, represent a hydrogen atom, an alkyl radical, a substituted alkyl radical, an aryl radical or a substituted aryl radical;

m may take the values of 0 or 1;

n may take the values of 0, 1 or 2;

p may take the values of 0, 1 or 2;

and also their addition salts with a pharmaceutically acceptable acid, their addition salts with a pharmaceutically acceptable base and the enantiomers of said compounds.

According to the present invention, the compounds of general formula (I) that are particularly preferred are those for which:

$R_1$ and $R_2$, which are identical or different, represent alkyl radicals or else they form a ring with the nitrogen atom to which they are attached, said ring being represented by the following formula:

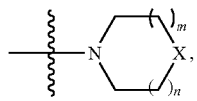

X, m and n having the meanings given below;

$R_3$ is a hydrogen atom or a lower alkyl radical;

$R_4$ is an alkynyl radical, a substituted alkynyl radical, an aryl radical, a substituted aryl radical, an aralkyl radical, a substituted aralkyl radical, a heterocyclic radical, a substituted heterocyclic radical, a heteroaryl radical, a substituted heteroaryl radical, a heteroaralkyl radical or a substituted heteroaralkyl radical;

X represents an oxygen atom, a —$CH_2$— radical or a —CH—($CH_2$)$_p$—$NR_5R_6$ radical, $R_5$, $R_6$ and p having the meanings given below;

$R_5$ and $R_6$, which may be identical or different, represent a hydrogen atom, an alkyl radical, a substituted alkyl radical, an aryl radical or a substituted aryl radical;

m takes the value of 1;

n may take the values of 0, 1 or 2;

p may take the values of 0, 1 or 2;

and also their addition salts with a pharmaceutically acceptable acid, their addition salts with a pharmaceutically acceptable base and the enantiomers of said compounds.

According to the present invention, the compounds of general formula (I) that are more particularly preferred are those for which:

$R_1$ and $R_2$ form a ring with the nitrogen atom to which they are attached, said ring being represented by the following formula:

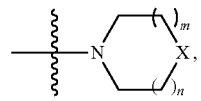

X, m and n having the meanings given below;

$R_3$ is a hydrogen atom;

$R_4$ is an aryl radical, a substituted aryl radical, an aralkyl radical, a substituted aralkyl radical, a heterocyclic radical, a substituted heterocyclic radical, a heteroaryl radical, a substituted heteroaryl radical, a heteroaralkyl radical or a substituted heteroaralkyl radical;

X represents an oxygen atom, a —$CH_2$— radical or a —CH—($CH_2$)$_p$—$NR_5R_6$ radical, $R_5$, $R_6$ and p having the meanings given below;

$R_5$ and $R_6$, which may be identical or different, represent a hydrogen atom, an alkyl radical, a substituted alkyl radical, an aryl radical or a substituted aryl radical;

m takes the value of 1;

n may take the values of 1 or 2;

p may take the values of 0, 1 or 2;

and also their addition salts with a pharmaceutically acceptable acid, their addition salts with a pharmaceutically acceptable base and the enantiomers of said compounds.

According to the present invention, the compounds of general formula (I) that are even more particularly preferred are those for which:

$R_1$ and $R_2$ form a ring with the nitrogen atom to which they are attached, said ring being represented by the following formula:

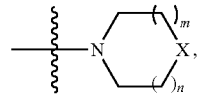

X, m and n having the meanings given below;

$R_3$ is a hydrogen atom;

$R_4$ is a heterocyclic radical, a substituted heterocyclic radical, a heteroaryl radical, a substituted heteroaryl radical, a heteroaralkyl radical or a substituted heteroaralkyl radical;

X represents an oxygen atom or a —$CH_2$— radical;

n takes the value of 1;

and also their addition salts with a pharmaceutically acceptable acid, their addition salts with a pharmaceutically acceptable base and the enantiomers of said compounds.

According to the present invention, the compounds of general formula (I) that are most particularly preferred are those for which:

$R_1$ and $R_2$ form a ring with the nitrogen atom to which they are attached, said ring being represented by the following formula:

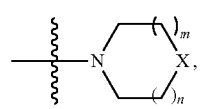

X, m and n having the meanings given below;

$R_3$ is a hydrogen atom;

$R_4$ is a heteroaryl radical or a substituted heteroaryl radical;

X represents an oxygen atom or a —$CH_2$— radical;

m takes the value of 1;

n takes the value of 1;

and also their addition salts with a pharmaceutically acceptable acid, their addition salts with a pharmaceutically acceptable base and the enantiomers of said compounds.

The compounds according to the invention have a very good TACE-inhibiting activity and in particular they inhibit the TACE enzyme selectively relative to other ADAMs and MMPs. This inhibiting activity of the TACE enzyme is measured in an enzymatic test and quantified by the measurement of an $IC_{50}$ (inhibitory concentration necessary to obtain 50% inhibition of the TACE enzyme), as described in example 12. The compounds of the present invention have an $IC_{50}$ for TACE of less than or equal to 10 μM and more particularly of less than or equal to 1 μM. Advantageously, the compounds of the present invention have an $IC_{50}$ for TACE of less than or equal to 0.5 μM.

Advantageously, these compounds are also very selective for TACE relative to the other ADAMs and MMPs (see example 13): their inhibitory activity is at least ten times greater for TACE than for other ADAMs and MMPs (that is to say that the value of the $IC_{50}$ for TACE is at least ten times smaller than that for other ADAMs and MMPs), and more advantageously at least 100 times greater.

TACE (TMFα-converting enzyme) catalyses the formation of soluble TNF-α from the precursor protein (transmembrane TNFα) bound to the membranes of certain cells. TNFα is a proinflammatory cytokine which is known for playing a role in numerous pathologies having an inflammatory nature.

The invention therefore targets the use of at least one compound of general formula (I) as defined above for the treatment of pathologies or disorders linked to a release of TNFα. An inhibitor of the TACE enzyme of general formula (I) reduces the production of TNFα. Therefore, it is of use for the treatment of pathologies linked to a release of TNFα.

The invention also targets the use of at least one compound of general formula (I) as defined above for the preparation of a pharmaceutical or cosmetic composition in which said compound has an inhibitory activity for the TACE enzyme.

Therefore it targets the use of at least one compound of general formula (I) as defined above for the treatment of pathologies or disorders which are improved by the inhibition of the TACE enzyme.

The invention also relates to a method of therapeutic (human or animal) treatment or cosmetic treatment that comprises the administration or application of a pharmaceutical or cosmetic composition comprising a compound of general formula (I) as an inhibitor of TACE and therefore as an inhibitor of the production of soluble TNFα.

Thus, the invention relates to the use of at least one compound of general formula (I) as defined above for the treatment of pathologies or disorders linked to TNFα production.

The invention also relates to the use of a compound of general formula (I) as defined above for the preparation of a medicament intended for the treatment of pathologies for which reducing the production of TNFα would be of great benefit.

Specifically, the compounds used according to the invention are particularly suitable for the treatment and prevention of disorders/diseases such as the inflammatory diseases that are listed below but that are not limiting, such as septic shock, haemodynamic shock, malaria, inflammatory bowel diseases (IBDs) such as Crohn's disease and ulcerative colitis, inflammatory bone diseases, mycobacterial infections, meningitis, fibrotic diseases, heart diseases, atherosclerosis, obesity, ischaemic attack, graft rejection, cancer, diseases involving angiogenesis phenomena, autoimmune diseases, osteoarthritis, rheumatoid arthritis, ankylosing spondylitis, chronic juvenile arthritis, multiple sclerosis, HIV, non-insulin-dependent diabetes mellitus, allergic diseases, asthma, chronic obstructive pulmonary disease (COPD), inflammatory diseases of the skin, psoriasis, atopic dermatitis and psoriatic arthritis.

These molecules are also potential active principles for the treatment of neurological pathologies having an inflammatory nature for which reducing the production of TNFα would be of great benefit. These pathologies listed below in a non-limiting manner are, for example, Alzheimer's disease, Parkinson's disease, Parkinsonian disorders, amyotrophic lateral sclerosis, autoimmune diseases of the nervous system, autonomic diseases of the nervous system, dorsal pains, cerebral oedema, cerebrovascular diseases, dementia, nerve fibre demyelinating autoimmune diseases of the nervous system, diabetic neuropathies, encephalitis, encephalomyelitis, epilepsy, chronic fatigue syndrome, giant cell arteritis, Guillain-Barré syndrome, headaches, multiple sclerosis, neuralgia, peripheral nervous system diseases, polyneuropathies, polyradiculoneuropathy, radiculopathy, respiratory paralyses, spinal cord diseases, Tourette syndrome, central nervous system vasculitis, Huntington's disease and cerebral attack.

The invention relates to the use of a compound of general formula (I) as defined above for the preparation of a medicament intended for the treatment of pathologies having an inflammatory nature in which TNFα is involved.

The invention also relates to the use of a compound of general formula (I) as defined above for the preparation of a medicament intended for the treatment of inflammatory diseases of the skin, and the treatment of psoriasis, atopic dermatitis or psoriatic arthritis.

Another subject of the present invention is a pharmaceutical composition intended, in particular, for the treatment of the aforementioned afflictions, and which is characterized by the fact that it comprises, in a pharmaceutically acceptable support that is compatible with the mode of administration used for this composition, at least one compound of general formula (I). This compound of general formula (I) may also be in one of its enantiomeric forms or in the form of one of its pharmaceutically acceptable salts.

Figure 1:
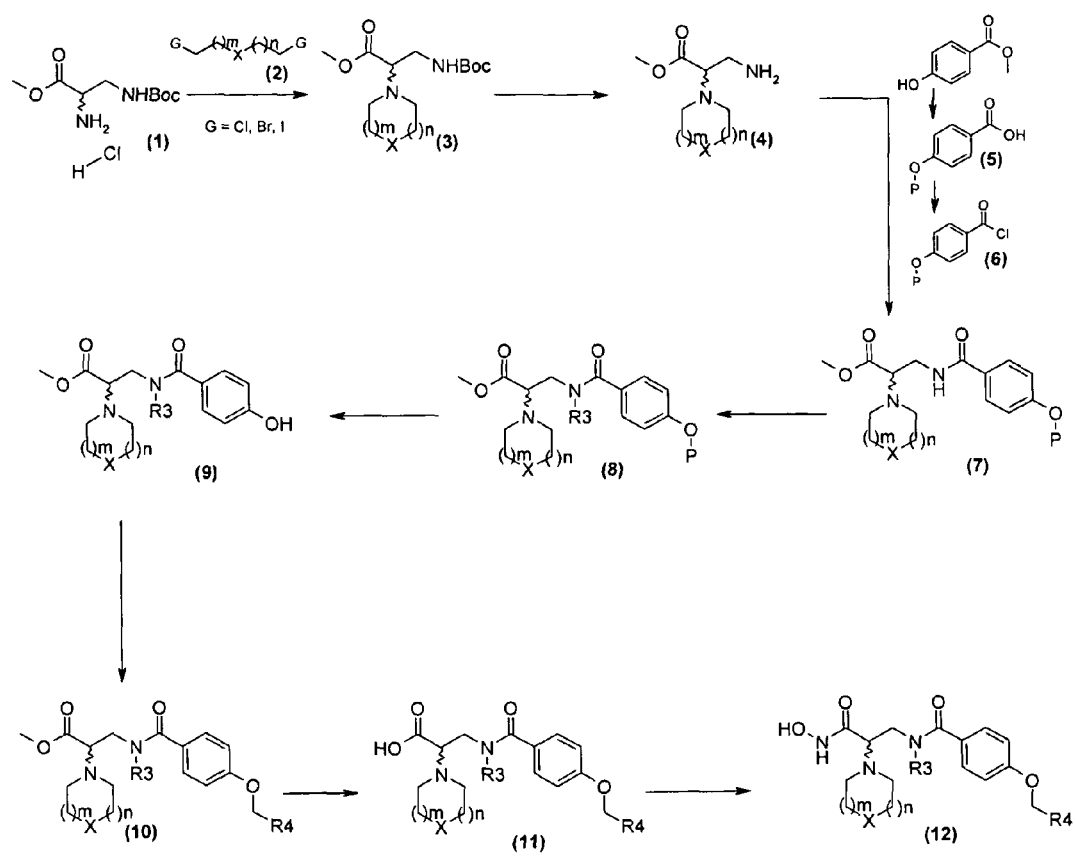
FIG. 1 shows the reaction scheme for preparing compound (12).
Figure 2:
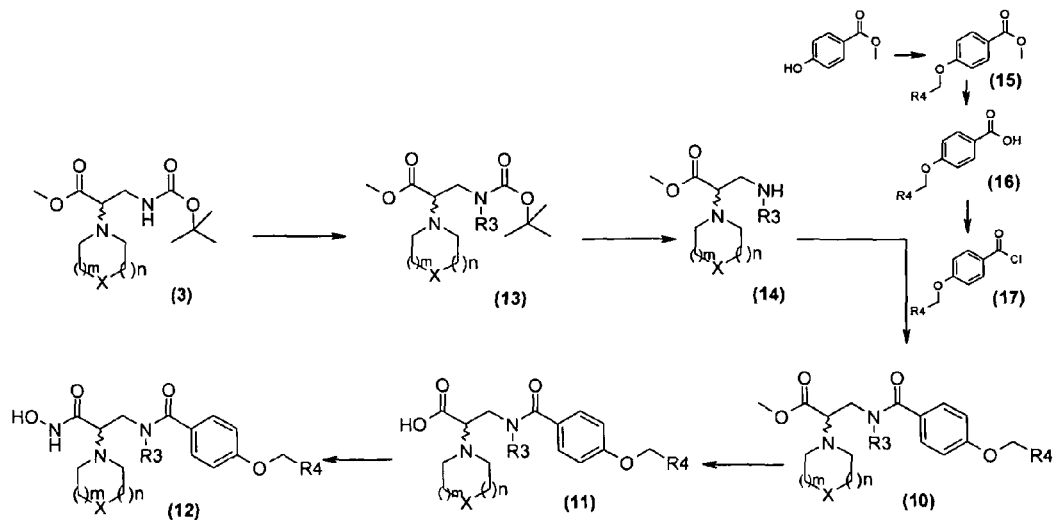
FIG. 2 shows an alternative reaction scheme for preparing compound (12).
Figure 3:
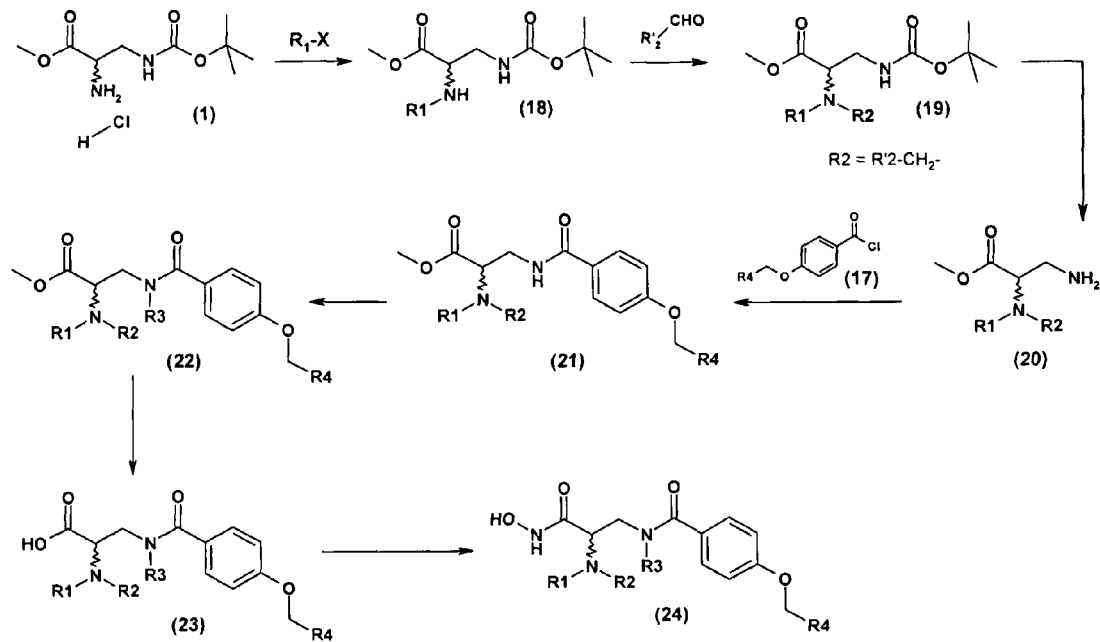
FIG. 3 shows the reaction scheme for preparing compound (24).

Several examples of the preparation of active compounds of formula (I) according to the invention, and also results of the biological activity of such compounds, will now be given by way of illustration and with no limiting character.

EXEMPLARY EMBODIMENTS

The compounds of general formula (I) are characterized by proton NMR analysis on an Advanced 400 MHz Bruker machine.

Example 1

4-but-2-ynyloxy-N—((S)-2-hydroxycarbamoyl-2-piperidin-1-ylethyl)benzamide 1-1: Methyl (S)-3-tert-butoxycarbonylamino-2-piperidin-1-ylpropanoate 1.8 ml (6.5 mmol) of triethylamine are added to a solution of 1 g (6.5 mmol) of commercial methyl (S)-2-amino-3-tertbutoxycarbonylaminopropanoate hydrochloride in 20 ml of tert-butanol. The reaction medium is stirred for 30 min at 40° C. then filtered. Added to the filtrate thus obtained are 1.2 ml (8.6 mmol) of 1,5-dibromopentane and the reaction medium is heated at 60° C. for 3 days. After filtration of the insoluble fraction, the filtrate is concentrated under vacuum. The crude residue is purified by chromatography over silica gel eluted with a 70/30 heptane/ethyl acetate mixture. 600 mg (49%) of methyl (S)-3-tert-butoxycarbonylamino-2-piperidin-1-yl-propanoate are obtained in the form of a colourless oil.

1-2: Methyl (S)-3-amino-2-piperidin-1-ylpropanoate dihydrochloride

A solution of 830 mg (2.8 mmol) of methyl (S)-3-tert-butoxycarbonylamino-2-piperidin-1-yl-propanoate in 15 ml of methanol and 3 ml of hydrochloric acid in isopropanol having a concentration of 5-6N is stirred at 40° C. for 18 h. After concentrating under vacuum, the residue is taken up in ethyl acetate, filtered and dried under vacuum. 630 mg (100%) of methyl (S)-3-amino-2-piperidin-1-ylpropanoate dihydrochloride are obtained in the form of a yellow solid.

1-3: Methyl 4-but-2-ynyloxybenzoate 13.6 g (98.5 mmol) of potassium carbonate then 9.6 g (65.7 mmol) of 1-bromobut-2-yne are added to a solution containing 10 g (65.7 mmol) of methyl 4-hydroxybenzoate diluted in 250 ml of 2-butanone. The reaction medium is stirred at reflux for 5 h then at ambient temperature for 18 h. After filtration of the salts, the filtrate is concentrated under vacuum. 13.4 g (100%) of methyl 4-but-2-ynyloxybenzoate are obtained in the form of a light-yellow solid.

1-4: 4-But-2-ynyloxybenzoic acid 26 ml (262 mmol) of an aqueous solution of sodium hydroxide having a concentration of 10N are added to a solution of 13.4 g (65.7 mmol) of methyl 4-but-2-ynyloxybenzoate diluted in 200 ml of tetrahydrofuran and 25 ml of water. The reaction medium is stirred at reflux for 5 h then at 45° C. for 18 h. The reaction medium is hydrolysed, diluted with ethyl acetate then brought to pH=6 using an aqueous solution of hydrochloric acid having a concentration of 1N. The product is extracted with ethyl acetate. The organic phase is washed with water then with a saturated aqueous solution of sodium chloride, dried over magnesium sulphate, filtered and concentrated.

12.5 g (100%) of 4-but-2-ynyloxybenzoic acid are obtained in the form of a white solid.

1-5: Methyl (S)-3-(4-but-2-ynyloxybenzoylamino)-2-cyclohexylpropanoate 420 mg (3.1 mmol) of 1-hydroxybenzotriazole and 600 mg (3.1 mmol) of 1-ethyl-3-(3-dimethylaminopropyl)-carbodiimide hydrochloride are added to a solution of 540 mg (3.1 mmol) of 4-but-2-ynyloxybenzoic acid in 10 ml of dimethylformamide. The reaction medium is stirred for 15 min at ambient temperature then 630 mg (2.8 mmol) of methyl (S)-3-amino-2-piperidin-1-yl-propanoate dihydrochloride in 10 ml of dimethylformamide and 0.8 ml (5.7 mmol) of triethylamine are added. The reaction medium is stirred at ambient temperature for 18 h. The organic phase is washed with an aqueous solution of sodium hydrogen carbonate then with a saturated aqueous solution of sodium chloride, dried over magnesium sulphate, filtered and concentrated. The crude product obtained is purified by chromatography over silica gel eluted with a 99/1 dichloromethane/methanol mixture. 580 mg (58%) of methyl (S)-3-(4-but-2-ynyloxybenzoylamino)-2-cyclohexylpropanoate are obtained in the form of a colourless oil.

1-6: (S)-3-(4-but-2-ynyloxybenzoylamino)-2-piperidin-1-ylpropanoic acid 2.5 ml (2.4 mmol) of an aqueous solution of lithium hydroxide having a concentration of 1N are added to a solution of 0.6 g (1.6 mmol) of methyl (S)-3-(4-but-2-ynyloxybenzoylamino)-2-piperidin-1-ylpropanoate in 10 ml of tetrahydrofuran. The reaction medium is then stirred at ambient temperature for 18 h. After evaporating the tetrahydrofuran under vacuum, 2.4 ml of an aqueous solution of hydrochloric acid having a concentration of 1N and water are added then the reaction medium is extracted with ethyl acetate. The organic phase is dried over magnesium sulphate, filtered and concentrated under vacuum. The residue obtained is purified by chromatography over silica gel eluted with a 90/10 dichloromethane/methanol mixture. 580 mg (100%) of (S)-3-(4-but-2-ynyloxybenzoylamino)-2-piperidin-1-ylpropanoic acid are obtained in the form of a white solid.

1-7: 4-but-2-ynyloxy-N—((S)-2-hydroxycarbamoyl-2-piperidin-1-ylethyl)benzamide 270 mg (2.0 mmol) of 1-hydroxybenzotriazole and 390 mg (2.0 mmol) of 1-ethyl-3-(3-dimethylaminopropyl)-carbodiimide hydrochloride are added successively to a solution of 580 mg (1.7 mmol) of (S)-3-(4-but-2-ynyloxybenzoylamino)-2-piperidin-1-ylpropanoic acid in 15 ml of dimethylformamide. The reaction medium is stirred for 30 min at ambient temperature then 300 mg (2.0 mmol) of O-tert-butyldimethylsilylhydroxylamine in 5 ml of dimethylformamide are added. After stirring at ambient temperature for 18 h then hydrolysis with 2 ml of an aqueous solution of 5% citric acid, the reaction medium is stirred at ambient temperature for a further 30 min, then extracted with ethyl acetate. The ethyl acetate phase is washed with a saturated aqueous solution of sodium hydrogen carbonate then with a saturated aqueous solution of sodium chloride, dried over magnesium sulphate, filtered and concentrated. The residue obtained is purified by chromatography over silica gel eluted with a 98/2 dichloromethane/methanol mixture. 80 mg (13%) of 4-but-2-ynyloxy-N—((S)-2-hydroxycarbamoyl-2-piperidin-1-ylethyl)benzamide are obtained in the form of a white solid having a melting point of 144° C.

$^1$H NMR (δ, DMSO): 1.30-1.50 (m, 6H); 1.80 (s, 3H); 2.47 (m, 2H); 2.55 (m, 2H); 3.19 (t, J=7.12 Hz, 1H); 3.40 (m, 1H), 3.48-3.56 (m, 1H); 4.79 (s, 2H); 7.00 (d, J=8.9 Hz, 2H); 7.79 (d, J=8.9 Hz, 2H); 8.20 (t, J=5.6 Hz, 1H); 8.80 (s, 1H); 10.49 (s, 1H).

Example 2

N—((S)-2-hydroxycarbamoyl-2-piperidin-1-ylethyl)-4-(2-methylquinolin-4-ylmethoxy)benzamide

2-1: Methyl 4-(2-methoxyethoxymethoxy)benzoate 3.2 g (78.9 mmol) of 60% sodium hydride are added to a solution of 10 g (65.7 mmol) of methyl 4 hydroxybenzoate in 50 ml of tetrahydrofuran and 50 ml of dimethylformamide. The reaction medium is stirred at ambient temperature for 20 minutes then 8.3 g (72.3 mmol) of 2-methoxyethoxymethyl chloride are added. After stirring for 24 h at ambient temperature, the mixture is poured over water then extracted with ethyl acetate. The organic phase is washed with water then with a saturated aqueous solution of sodium chloride, dried over magnesium sulphate, filtered and concentrated. 16 g (100%) of methyl 4-(2-methoxyethoxymethoxy)benzoate are obtained in the form of a colourless oil.

2-2: 4-(2-Methoxyethoxymethoxy)benzoic acid 15 g (375 mmol) of sodium hydroxide powder are added to a solution of 16 g (75 mmol) of methyl 4-(2-methoxyethoxymethoxy)benzoate in 250 ml of tetrahydrofuran, 80 ml of water and 30 ml of methanol. The reaction medium is stirred at 40° C. for 18 h then hydrolysed, diluted with ethyl acetate and brought to pH=6 with an aqueous solution of hydrochloric acid having a concentration of 1N. After extracting with ethyl acetate, the organic phase is washed with water then with a saturated aqueous solution of sodium chloride, dried over magnesium sulphate, filtered then concentrated. 16 g (95%) of 4-(2-methoxyethoxymethoxy)benzoic acid are obtained in the form of a white solid.

2-3: Methyl (S)-3-[4-(2-methoxyethoxymethoxy) benzoylamino]-2-piperidin-1-ylpropanoate In a manner similar to Example 1.5, starting from 6.7 g (29.7 mmol) of 4-(2-methoxyethoxymethoxy)benzoic acid and from 7 g (27 mmol) of methyl (S)-3-amino-2-piperidin-1-ylpropanoate dihydrochloride (prepared as described in Example 12-2), 9.6 g (90%) of methyl (S)-3-[4-(2-methoxyethoxymethoxy)benzoylamino]-2-piperidin-1-ylpropanoate are obtained in the form of a colourless oil.

2-4: Methyl (S)-3-(4-hydroxybenzoylamino)-2-piperidin-1-ylpropanoate 1.5 ml of 98% sulphuric acid are added to a solution of 9.6 g (24.3 mmol) of methyl (S)-3-[4-(2-methoxyethoxymethoxy)benzoylamino]-2-piperidin-1-yl-propanoate in 50 ml of tetrahydrofuran and 50 ml of methanol. The reaction medium is then stirred at 35° C. for 18 h. The solvents are concentrated under vacuum to 80% then the residue is taken up in ethyl acetate and hydrolysed. The pH is brought to 8 with a saturated aqueous solution of sodium hydrogen carbonate. The product is extracted with ethyl acetate. The organic phase is washed with water then with a saturated aqueous solution of sodium chloride, dried over magnesium sulphate, filtered and concentrated under vacuum. 6.9 g (93%) of methyl (S)-3-(4-hydroxybenzoylamino)-2-piperidin-1-ylpropanoate are obtained in the form of a white solid.

2-5: Methyl (S)-3-[4-(2-methylquinolin-4-ylmethoxy)benzoylamino]-2-piperidin-1-ylpropanoate 270 mg (1.9 mmol) of potassium carbonate then 380 mg (1.9 mmol) of 4-chloromethyl-2-methylquinoline and 15 mg of potassium iodide are added to a solution of 500 mg (1.6 mmol) of methyl (S)-3-(4-hydroxybenzoyl-amino)-2-piperidin-1-ylpropanoate in 15 ml of 2-butanone. The reaction medium is stirred at 80° C. for 18 h. After filtration, the filtrate is concentrated under vacuum. The crude product is purified by chromatography over silica gel eluted with a 50/50 heptane/ethyl acetate mixture. 620 mg (83%) of methyl (S)-3-[4-(2-methylquinolin-4-ylmethoxy)benzoylamino]-2-piperidin-1-ylpropanoate are obtained in the form of a yellow solid.

2-6: (S)-3-[4-(2-methylquinolin-4-ylmethoxy)benzoylamino]-2-piperidin-1-ylpropanoic acid In a manner similar to Example 1.6, starting from 620 mg (1.3 mmol) of methyl (S)-3-[4-(2-methylquinolin-4-ylmethoxy)benzoylamino]-2-piperidin-1-ylpropanoate, 530 mg (88%) of (S)-3-[4-(2-methylquinolin-4-yl-methoxy)benzoylamino]-2-piperidin-1-ylpropanoic acid are obtained in the form of a beige solid.

2-7: N—((S)-2-hydroxycarbamoyl-2-piperidin-1-ylethyl)-4-(2-methylquinolin-4-ylmethoxy)benzamide In a manner similar to Example 1.7, starting from 0.5 g (1.2 mmol) of (S)-3-[4-(2-methylquinolin-4-ylmethoxy)benzoylamino]-2-piperidin-1-ylpropanoic acid, 150 mg (28%) of N—((S)-2-hydroxycarbamoyl-2-piperidin-1-yl-ethyl)-4-(2-methylquinolin-4-ylmethoxy)benzamide are obtained in the form of a white solid having a melting point of 190° C.
$^1$H NMR (δ, DMSO): 1.15 (m, 2H); 1.30 (m, 4H); 2.25 (m, 2H); 2.38 (m, 2H); 2.50 (s, 3H); 3.04 (t, J=6.8 Hz, 1H); 3.25 (m, 1H); 3.37 (m, 1H); 5.52 (s, 2H); 7.05 (d, J=8.8 Hz, 2H); 7.40 (s, 1H); 7.44 (t, J=7.3 Hz, 1H); 7.57 (t, J=6.8 Hz, 1H); 7.68 (d, J=8.8 Hz, 2H); 7.81 (d, J=8.3 Hz, 1H); 7.95 (d, J=8.3 Hz, 1H); 8.07 (m, 1H); 8.65 (s, 1H); 10.34 (s, 1H).

Example 3

4-(2,6-dichloropyridin-4-ylmethoxy)-N—((S)-2-hydroxycarbamoyl-2-piperidin-1-ylethyl)benzamide

3-1: Methyl (S)-3-[4-(2,6-dichloropyridin-4-yl-methoxy)benzoylamino]-2-piperidin-1-ylpropanoate 500 mg (1.6 mmol) of methyl (S)-3-(4-hydroxybenzoyl-amino)-2-piperidin-1-ylpropanoate (prepared as described in Example 2.4), 320 mg (1.8 mmol) of 2,6-dichloropyridin-4-yl)methanol and 850 mg (3.3 mmol) of triphenylphosphine are put into solution in 15 ml of tetrahydrofuran then 0.5 ml (3.3 mmol) of diethyl azodicarboxylate are added. The reaction medium is stirred at ambient temperature for 18 h then 1 ml (6.6 mmol) of diethyl azodicarboxylate are again added. After stirring for 30 h, the mixture is concentrated and diethyl ether is added. After filtration and evaporation of the filtrate, the residue is purified by chromatography over silica gel eluted with a 70/30 heptane/ethyl acetate mixture. 200 mg (26%) of methyl (S)-3-[4-(2,6-dichloropyridin-4-yl-methoxy)benzoyl-amino-]-2-piperidin-1-ylpropanoate are obtained in the form of a colourless oil.

3-2: (S)-3-[4-(2,6-dichloropyridin-4-yl-methoxy)benzoylamino]-2-piperidin-1-ylpropanoic acid In a manner similar to Example 1.6, starting from 200 mg (0.4 mmol) of methyl (S)-3-[4-(2,6-dichloropyridin-4-yl-methoxy)benzoylamino]-2-piperidin-1-ylpropanoate, 164 mg (86%) of (S)-3-[4-(2,6-dichloropyridin-4-ylmethoxy)benzoylamino]-2-piperidin-1-ylpropanoic acid are obtained in the form of a white solid.

3-3: 4-(2,6-dichloropyridin-4-ylmethoxy)-N—((S)-2-hydroxycarbamoyl-2-piperidin-1-ylethyl)benzamide In a manner similar to Example 1.7, starting from 164 mg (0.7 mmol) of (S)-3-[4-(2,6-dichloropyridin-4-ylmethoxy)

benzoylamino]-2-piperidin-1-ylpropanoic acid, 600 mg (36%) of 4-(2,6-dichloropyridin-4-ylmethoxy)-N—((S)-2-hydroxycarbamoyl-2-piperidin-1-ylethyl)benzamide are obtained in the form of a beige solid having a melting point of 145° C.

$^1$H NMR (δ, DMSO): 1.33-1.36 (m, 2H); 1.36-1.50 (m, 4H); 2.48 (m, 2H); 2.55 (m, 2H); 3.19 (t, J=7.12 Hz, 1H); 3.36-3.42 (m, 1H); 3.47-3.60 (m, 1H); 5.29 (s, 2H); 7.09 (d, J=8.8 Hz, 2H); 7.62 (s, 2H); 7.82 (d, J=8.8 Hz, 2H); 8.23 (t, J=5 Hz, 1H); 8.81 (s, 1H); 10.49 (s, 1H).

Example 4

N—((S)-2-hydroxycarbamoyl-2-piperidin-1-ylethyl)-4-(2-phenylpyridin-4-ylmethoxy)benzamide 4-1: Methyl (S)-3-[4-(2-phenylpyridin-4-ylmethoxy)benzoylamino]-2-piperidin-1-ylpropanoate In a manner similar to Example 3-1, starting from 500 mg (1.6 mmol) of methyl (S)-3-(4-hydroxybenzoylamino)-2-piperidin-1-ylpropanoate (prepared as described in Example 2-4) and from 420 mg (2.3 mmol) of (2-phenylpyridin-4-yl)methanol, 285 mg (37%) of methyl (S)-3-[4-(2-phenylpyridin-4-ylmethoxy)benzoylamino]-2-piperidin-1-ylpropanoate are obtained in the form of a colourless oil.

4-2: (S)-3-[4-(2-phenylpyridin-4-ylmethoxy)benzoylamino]-2-piperidin-1-ylpropanoic acid In a manner similar to Example 1.6, starting from 285 mg (0.6 mmol) of methyl (S)-3-[4-(2-phenylpyridin-4-ylmethoxy)benzoylamino]-2-piperidin-1-ylpropanoate, 120 mg (44%) of (S)-3-[4-(2-phenylpyridin-4-yl-methoxy)-benzoyl-amino]-2-piperidin-1-ylpropanoic acid are obtained in the form of a white solid.

4-3: N—((S)-2-hydroxycarbamoyl-2-piperidin-1-ylethyl)-4-(2-phenylpyridin-4-ylmethoxy)benzamide In a manner similar to Example 1.7, starting from 120 mg (0.3 mmol) of (S)-3-[4-(2-phenylpyridin-4-yl-methoxy)-benzoylamino]-2-piperidin-1-ylpropanoic acid, 60 mg (49%) of N—((S)-2-hydroxycarbamoyl-2-piperidin-1-ylethyl)-4-(2-phenylpyridin-4-ylmethoxy)benzamide are obtained in the form of a white solid having a melting point of 177° C.

$^1$H NMR (δ, DMSO): 1.24 (m, 2H); 1.34 (m, 4H); 2.30 (m, 2H); 2.45 (m, 2H); 3.07 (t, J=7.2 Hz, 1H); 3.25 (m, 1H); 3.40 (m, 1H); 5.21 (s, 2H); 7.00 (d, J=8.8 Hz, 2H); 7.20 (d, J=5.4 Hz, 1H); 7.30 (m, 1H); 7.40 (m, 2H); 7.70 (m, 2H); 7.90 (s, 1H); 8.00 (d, J=7.1 Hz, 2H); 8.10 (t, J=5.3 Hz, 1H); 8.56 (d, J=5 Hz, 1H); 8.68 (s, 1H); 10.38 (s, 1H).

Example 5

N—((S)-2-hydroxycarbamoyl-2-piperidin-1-ylethyl)-4-(pyridin-4-ylmethoxy)benzamide 5-1: Methyl (S)-2-piperidin-1-yl-3-[4-(pyridin-4-ylmethoxy)benzoylamino]propanoate In a manner similar to Example 2-5, starting from 500 mg (1.6 mmol) of methyl (S)-3-(4-hydroxybenzoylamino)-2-piperidin-1-ylpropanoate (prepared as described in Example 2-4) and from 320 mg (1.9 mmol) of 4-chloromethylpyridine hydrochloride, 530 mg (81%) of methyl (S)-2-piperidin-1-yl-3-[4-(pyridin-4-yl-methoxy)-benzoyl-amino]propanoate are obtained in the form of a colourless oil.

5-2: (S)-2-piperidin-1-yl-3-[4-(pyridin-4-ylmethoxy)benzoylamino]propanoic acid

In a manner similar to Example 1-6, starting from 530 mg (1.3 mmol) of methyl (S)-2-piperidin-1-yl-3-[4-(pyridin-4-ylmethoxy)benzoylamino]propanoate, 550 mg (100%) of (S)-2-piperidin-1-yl-3-[4-(pyridin-4-ylmethoxy)-benzoylamino]propanoic acid are obtained in the form of a beige solid.

5-3: N—((S)-2-hydroxycarbamoyl-2-piperidin-1-ylethyl)-4-(pyridin-4-ylmethoxy)benzamide In a manner similar to Example 1-7, starting from 510 mg (1.3 mmol) of (S)-2-piperidin-1-yl-3-[4-(pyridin-4-ylmethoxy)benzoylamino]propanoic acid, 70 mg (13%) of N—((S)-2-hydroxycarbamoyl-2-piperidin-1-ylethyl)-4-(pyridin-4-ylmethoxy)benzamide are obtained in the form of a beige solid having a melting point of 190° C.

$^1$H NMR (δ, DMSO): 1.20 (m, 2H); 1.30 (m, 2H); 1.45 (m, 2H); 2.51 (m, 2H); 2.57 (m, 2H); 3.23 (m, 1H); 3.50-3.60 (m, 2H); 5.29 (s, 2H); 7.10 (d, J=8.8 Hz, 2H); 7.47 (d, J=4.3 Hz, 2H); 7.84 (d, J=8.7 Hz, 2H); 8.25 (s, 1H); 8.62 (m, 2H); 8.85 (m, 1H); 10.56 (s, 1H).

Example 6

4-(4-cyanobenzyloxy)-N—((S)-2-hydroxy-carbamoyl-2-piperidin-1-ylethyl)benzamide 6-1: Methyl (S)-3-[4-(4-cyanobenzyloxy)benzoylamino]-2-piperidin-1-ylpropanoate In a manner similar to Example 2-5, starting from 500 mg (1.6 mmol) of methyl (S)-3-(4-hydroxy-benzoylamino)-2-piperidin-1-ylpropanoate (prepared as described in Example 2-4) and from 350 mg (1.8 mmol) of 4-bromomethylbenzonitrile, 680 mg (98%) of methyl (S)-3-[4-(4-cyanobenzyloxy)benzoylamino]-2-piperidin-1-yl-propanoate are obtained in the form of a white solid.

6-2: (S)-3-[4-(4-cyanobenzyloxy)benzoylamino]-2-piperidin-1-ylpropanoic acid

In a manner similar to Example 1-6, starting from 680 mg (1.6 mmol) of methyl (S)-3-[4-(4-cyanobenzyloxy)benzoylamino]-2-piperidin-1-yl-propanoate, 590 mg (91%) of (S)-3-[4-(4-cyanobenzyloxy)benzoylamino]-2-piperidin-1-ylpropanoic acid are obtained in the form of a white solid.

6-3: 4-(4-cyanobenzyloxy)-N—((S)-2-hydroxycarbamoyl-2-piperidin-1-ylethyl)benzamide In a manner similar to Example 1-7, starting from 590 mg of (S)-3-[4-(4-cyanobenzyloxy)benzoylamino]-2-piperidin-1-ylpropanoic acid, 100 mg (16%) of 4-(4-cyanobenzyloxy)-N—((S)-2-hydroxycarbamoyl-2-piperidin-1-ylethyl)benzamide are obtained in the form of a white solid having a melting point of 134° C.

$^1$H NMR (δ, DMSO): 1.35 (m, 2H); 1.45 (m, 4H); 2.48 (m, 2H); 2.55 (m, 2H); 3.19 (t, J=6.9 Hz, 1H); 3.40 (m, 1H); 3.52 (m, 1H); 5.29 (s, 2H); 7.07 (d, J=8.8 Hz, 2H); 7.65 (d, J=8.2

Hz, 2H); 7.80 (d, J=8.8 Hz, 2H); 7.88 (d, J=8.2 Hz, 2H); 8.21 (s, 1H); 8.80 (s, 1H); 10.49 (s, 1H).

Example 7

N—((S)-2-hydroxycarbamoyl-2-piperidin-1-yl-ethyl)-4-(4-methylnaphthalen-1-ylmethoxy)benzamide

7-1: Methyl (S)-3-[4-(4-methylnaphthalen-1-yl-methoxy)-benzoylamino]-2-piperidin-1-ylpropanoate In a manner similar to Example 19-1, starting from 500 mg (1.6 mmol) of methyl (S)-3-(4-hydroxybenzoylamino)-2-piperidin-1-ylpropanoate (prepared as described in Example 2-4) and from 370 mg (1.9 mmol) of 1-chloromethyl-4-methylnaphthalene, 700 mg (93%) of methyl (S)-3-[4-(4-methylnaphthalen-1-yl-methoxy)benzoylamino]-2-piperidin-1-ylpropanoate are obtained in the form of a white solid.

7-2: (S)-3-[4-(4-methylnaphthalen-1-ylmethoxy)benzoylamino]-2-piperidin-1-ylpropanoic acid In a manner similar to Example 1-6, starting from 700 mg (1.5 mmol) of methyl (S)-3-[4-(4-methylnaphthalen-1-ylmethoxy)benzoylamino]-2-piperidin-1-ylpropanoate, 645 mg (95%) of (S)-3-[4-(4-methylnaphthalen-1-ylmethoxy)benzoylamino]-2-piperidin-1-ylpropanoic acid are obtained in the form of a white solid.

7-3: N—((S)-2-hydroxycarbamoyl-2-piperidin-1-ylethyl)-4-(4-methylnaphthalen-1-ylmethoxy)benzamide In a manner similar to Example 1-7, starting from 645 mg (1.4 mmol) of (S)-3-[4-(4-methylnaphthalen-1-yl-methoxy)-benzoylamino]-2-piperidin-1-ylpropanoic acid, 60 mg (10%) of N—((S)-2-hydroxycarbamoyl-2-piperidin-1-ylethyl)-4-(4-methylnaphthalen-1-ylmethoxy)benzamide are obtained in the form of a white solid having a melting point of 123° C.

$^1$H NMR (δ, DMSO): 1.34 (m, 2H); 1.45 (m, 4H); 2.48 (m, 2H); 2.54 (m, 2H); 2.67 (s, 3H); 3.20 (m, 1H); 3.39 (m, 1H); 3.55 (m, 1H); 5.57 (s, 2H); 7.15 (d, J=8.8 Hz, 2H); 7.37 (d, J=7.2 Hz, 1H); 7.57-7.63 (m, 3H); 7.82 (d, J=8.7 Hz, 2H); 8.07-8.10 (m, 2H); 8.21 (m, 1H); 8.80 (s, 1H); 10.50 (s, 1H).

Example 8

4-(2-bromopyridin-4-ylmethoxy)-N—((S)-2-hydroxycarbamoyl-2-piperidin-1-ylethyl)benzamide

8-1: Methyl (S)-3-[4-(2-bromopyridin-4-ylmethoxy)benzoylamino]-2-piperidin-1-ylpropanoate In a manner similar to Example 3-1, starting from 500 mg (1.6 mmol) of methyl (S)-3-[4-(2-methoxy-ethoxy-methoxy)benzoylamino]-2-piperidin-1-yl-propanoate (prepared as described in Example 2-4) and from 340 mg (1.8 mmol) of (2-bromopyridin-4-yl)methanol, 500 mg (40%) of methyl (S)-3-[4-(2-bromo-pyridin-4-ylmethoxy)benzoylamino]-2-piperidin-1-yl-propanoate are obtained in the form of a white solid.

8-2: (S)-3-[4-(2-bro=pyridin-4-ylmethoxy)benzoylamino]-2-piperidin-1-ylpropanoic acid In a manner similar to Example 1-6, starting from 500 mg (1.1 mmol) of methyl(S)-3-[4-(2-bromopyridin-4-ylmethoxy)benzoylamino]-2-piperidin-1-ylpropanoate, 185 mg (25%) of (S)-3-[4-(2-bromopyridin-4-ylmethoxy)benzoyl-amino]-2-piperidin-1-ylpropanoic acid are obtained in the form of a white solid.

8-3: 4-(2-bromopyridin-4-ylmethoxy)-N—((S)-2-hydroxy-carbamoyl-2-piperidin-1-ylethyl)benzamide 130 mg (0.4 mmol) of O-(benzotriazol-1-yl)-N,N,N',N'-tetramethyluronium tetrafluoroborate and 0.2 ml (1.2 mmol) of diisopropylethylamine are added to a solution of 185 mg (0.4 mmol) of (S)-3-[4-(2-bromopyridin-4-ylmethoxy)benzoylamino]-2-piperidin-1-ylpropanoic acid in 10 ml of dimethylformamide. After stirring for 20 minutes at ambient temperature, 65 mg (0.4 mmol) of O-tert-butyldimethysilylhydroxylamine diluted in 3 ml of dimethylformamide are added. The reaction medium is stirred at ambient temperature for 18 h, then hydrolysed with 1 ml of an aqueous solution of 5% citric acid and 2 ml of water. After stirring at ambient temperature for 1 h, the mixture is brought to pH=8 with a saturated aqueous solution of sodium hydrogen carbonate then extracted with ethyl acetate. The organic phase is washed with a saturated aqueous solution of sodium chloride, dried over magnesium sulphate, filtered and concentrated under vacuum. The crude product obtained is precipitated in an 8/2 heptane/ethyl acetate mixture then filtered. The residue obtained is recrystallized in ethyl acetate. 20 mg (10%) of 4-(2-bromopyridin-4-yl-methoxy)-N—((S)-2-hydroxycarbamoyl-2-piperidin-1-yl-ethyl)benzamide are obtained in the form of a pale-yellow solid having a melting point of 150° C.

$^1$H NMR (δ, DMSO): 1.35 (m, 2H); 1.45 (m, 4H); 2.48 (m, 2H); 2.58 (m, 2H); 3.19 (t, J=7.2 Hz, 1H); 3.40 (m, 1H); 3.53 (m, 1H); 5.27 (s, 2H); 7.08 (d, J=8.6 Hz, 2H); 7.49 (d, J=4.9 Hz, 1H); 7.71 (s, 1H); 7.81 (d, J=8.6 Hz, 2H); 8.22 (m, 1H); 8.40 (d, J=5 Hz, 1H); 8.81 (m, 1H); 10.50 (m, 1H).

Example 9

N—((S)-2-hydroxycarbamoyl-2-morpholin-4-yl-ethyl)-4-(pyridin-4-ylmethoxy)benzamide

9-1: Methyl (S)-3-tert-butoxycarbonylamino-2-morpholin-4-ylpropanoate

In a Schlenk tube, a solution of 10 g (39.3 mmol) of methyl (S)-2-amino-3-tert-butoxy-carbonyl-aminopropanoate hydrochloride and 5.6 g (39.3 mmol) of 1-chloro-2-(2-chloroethoxy)ethane in 65 ml of N,N-diisopropyl-ethylamine is heated at 127° C. with vigorous stirring for 18 h. After addition of water, the product is extracted with ethyl acetate. The organic phases are combined, washed with water, dries over magnesium sulphate, filtered and concentrated under vacuum. The crude product obtained is purified by chromatography over silica gel eluted with a 50/50 heptane/ethyl acetate mixture. 5.6 g (39%) of methyl (S)-3-tert-butoxycarbonylamino-2-(4-methanesulphonylpiperazin-1-yl)propanoate are obtained in the form of a yellow oil.

9-2: Methyl (S)-3-amino-2-morpholin-4-ylpropanoate dihydrochloride

In a manner similar to Example 1-2, starting from 5.6 g (19.4 mmol) of methyl (S)-3-tert-butoxycarbonylamino-2-morpholin-4-ylpropanoate, 4.3 g (97%) of methyl (S)-3- amino-2-morpholin-4-ylpropanoate dihydrochloride are obtained in the form of a beige solid.

9-3: Methyl (S)-3-[4-(2-methoxyethoxymethoxy) benzoylamino]-2-morpholin-4-ylpropanoate In a manner similar to Example 1-5, starting from 2.3 g (8.8 mmol) of methyl (S)-3-amino-2-morpholin-4-ylpropanoate dihydrochloride and from 2.2 g (9.7 mmol) of 4-(2-methoxy-ethoxymethoxy)benzoic acid (prepared as described in Example 2-2), 2.7 g (79%) of methyl (S)-3-[4-(2-methoxy-ethoxymethoxy)benzoylamino]-2-morpholin-4-ylpropanoate are obtained in the form of a yellow oil.

9-4: Methyl (S)-3-(4-hydroxybenzoylamino)-2-morpholin-4-ylpropanoate

In a manner similar to Example 2-4, starting from 2.7 g (6.9 mmol) of methyl (S)-3-[4-(2-methoxyethoxymethoxy)benzoylamino]-2-morpholin-4-yl-propanoate, 1.8 g (86%) of methyl (S)-3-(4-hydroxy-benzoylamino)-2-morpholin-4-yl-propanoate are obtained in the form of a white solid.

9-5: Methyl (S)-2-morpholin-4-yl-3-[4-(pyridin-4-ylmethoxy)benzoylamino]propanoate In a manner similar to Example 2-5, starting from 300 mg (1.0 mmol) of methyl (S)-3-(4-hydroxybenzoylamino)-2-morpholin-4-ylpropanoate and from 176 mg (1.1 mmol) of 4-(chloromethyl)pyridine chloride, 241 mg (62%) of methyl (S)-2-morpholin-4-yl-3-[4-(pyridin-4-ylmethoxy)benzoylamino]propanoate are obtained in the form of a yellow oil.

9-6: (S)-2-morpholin-4-yl-3-[4-(pyridin-4-ylmethoxy)benzoylamino]propanoic acid In a manner similar to Example 1-6, starting from 234 mg (0.6 mmol) of methyl (S)-2-morpholin-4-yl-3-[4-(pyridin-4-ylmethoxy)benzoylamino]propanoate, 154 mg (68%) of (S)-2-morpholin-4-yl-3-[4-(pyridin-4-yl-methoxy)-benzoylamino]propanoic acid are obtained in the form of a white solid.

9-7: N—((S)-2-hydroxycarbamoyl-2-morpholin-4-ylethyl)-4-(pyridin-4-ylmethoxy)benzamide In a manner similar to Example 1-7, starting from 158 mg (0.4 mmol) of (S)-2-morpholin-4-yl-3-[4-(pyridin-4-ylmethoxy)benzoylamino]propanoic acid, 90 mg (23%) of N—((S)-2-hydroxycarbamoyl-2-morpholin-4-yl-ethyl)-4-(pyridin-4-ylmethoxy)benzamide are obtained in the form of a beige powder.

$^1$H NMR (δ, DMSO): 2.54-2.60 (m, 4H); 3.21 (m, 1H); 3.39 (m, 1H); 3.53 (m, 4H); 3.70 (m, 1H); 5.26 (s, 2H); 7.08 (d, J=8.7 Hz, 2H); 7.44 (d, J=4 Hz, 2H); 8.30 (m, 2H); 8.59 (d, J=5.4 Hz, 2H); 8.87 (s, 1H); 10.59 (s, 1H).

Example 10

N—((S)-2-hydroxycarbamoyl-2-morpholin-4-yl-ethyl)-4-[2-(3-trifluoromethylphenyl)pyridin-4-yl-methoxy]benzamide

10-1: [2-(2-trifluoromethylphenyl)pyridin-4-yl]methanol 16.5 ml (0.3 mmol) of an aqueous solution of potassium carbonate having a concentration of 2M and 0.4 g (0.1 mmol) of 1,1'-bis(diphenylphosphino)ferrocene palladium(II) dihydrochloride are added under a stream of nitrogen to a solution containing 2.0 g (0.1 mmol) of 2-bromopyridine-4-methanol and 2.2 g (0.1 mmol) of 2-(trifluoromethyl)phenylboronic acid in 30 ml of toluene. The mixture is stirred at 80° C. for 5 hours then 20 ml of water are added. After extraction with ethyl acetate, the organic phase is dried over sodium sulphate, filtered and evaporated. The residue obtained is purified by chromatography over silica gel eluted with a 60/40 heptane/ethyl acetate mixture. 2.3 g (85%) of [2-(2-trifluoromethylphenyl)pyridin-4-yl]methanol are obtained in the form of a yellow oil.

10-2: Methyl (S)-2-morpholin-4-yl-3-{4-[2-(2-trifluoromethylphenyl)pyridin-4-ylmethoxy]benzoylamino}propanoate In a manner similar to Example 3-1, starting from 400 mg (0.9 mmol) of methyl (S)-3-(4-hydroxybenzoylamino)-2-morpholin-4-ylpropanoate (prepared as described in Example 9-4) and from 228 mg (0.9 mmol) of [2-(2-trifluoromethylphenyl)pyridin-4-yl]methanol, 344 mg (49%) of methyl (S)-2-morpholin-4-yl-3-{4-[2-(2-trifluoromethylphenyl)pyridin-4-yl-methoxy]benzoylamino}-propanoate are obtained in the form of a white solid.

10-3: (S)-2-morpholin-4-yl-3-{4-[2-(2-trifluoromethyl-phenyl)pyridin-4-ylmethoxy]benzoylamino}propanoic acid In a manner similar to Example 1-6, starting from 343 mg (0.6 mmol) of methyl (S)-2-morpholin-4-yl-3-{4-[2-(2-trifluoromethylphenyl)pyridin-4-ylmethoxy]-benzoylamino}propanoate, 313 mg (94%) of (S)-2-morpholin-4-yl-3-{4-[2-(2-trifluoromethylphenyl)-pyridin-4-ylmethoxy]benzoylamino}propanoic acid are obtained in the form of a pale-yellow solid.

10-4: N—((S)-2-hydroxycarbamoyl-2-morpholin-4-ylethyl)-4-[2-(2-trifluoromethylphenyl)pyridin-4-ylmethoxy]benzamide In a manner similar to Example 1-7, starting from 153 mg (0.3 mmol) of (S)-2-morpholin-4-yl-3-{4-[2-(2-trifluoromethylphenyl)pyridin-4-ylmethoxy]-benzoyl-amino}propanoic acid, 108 mg (69%) of N—((S)-2-hydroxycarbamoyl-2-morpholin-4-ylethyl)-4-[2-(2-trifluoromethylphenyl)pyridin-4-ylmethoxy]benzamide are obtained in the form of a white powder having a melting point of 151 C.

$^1$H NMR (δ, DMSO): 2.56 (m, 4H); 3.20 (t, J=7 Hz, 1H); 3.40 (m, 1H); 3.55 (m, 5H); 5.33 (s, 2H); 7.10 (d, J=8.8 Hz, 2H); 7.49 (d, J=5 Hz, 1H); 7.54 (m, 2H); 7.68 (m, 1H); 7.81 (m, 4H); 8.29 (t, J=5.6 Hz, 1H); 8.66 (d, J=5 Hz, 1H); 8.87 (s, 1H); 10.59 (s, 1H).

Example 11

N—((S)-2-diethylamino-2-hydroxycarbamoyl-ethyl)-4-(2-methylquinolin-4-ylmethoxy)benzamide

11-1: Methyl (S)-3-tert-butoxycarbonylamino-2-ethyl-aminopropanoate

In a manner similar to Example 1-1, starting from 500 mg (2 mmol) of methyl (S)-2-amino-3-tert-butoxy-carbonyl-aminopropanoate hydrochloride and from 870 mg (6.3 mmol) of iodoethane, 192 mg (40%) of methyl (S)-3-tert-butoxycarbonylamino-2-ethylaminopropanoate are obtained in the form of a yellow oil.

11-2: Methyl (S)-3-tert-butoxycarbonylamino-2-diethylaminopropanoate

150 µl (2.4 mmol) of acetaldehyde are added to 369 mg (1.5 mmol) of methyl (S)-3-tert-butoxycarbonylamino-2-ethylaminopropanoate in 5 ml of tetrahydrofuran then stirred for 30 minutes at ambient temperature. After cooling to 0° C., 189 mg (3 mmol) of sodium cyanoborohydride are added and the reaction medium is stirred at ambient temperature for 36 h. Water is added and the medium is extracted with ethyl acetate. The organic phase is washed with water, dried over magnesium sulphate, filtered then concentrated. The crude residue obtained is purified by chromatography over silica gel eluted with a 70/30 heptane/ethyl acetate mixture. 150 mg (38%) of methyl (S)-3-tert-butoxycarbonylamino-2-diethylaminopropanoate are obtained in the form of a colourless oil.

11-3: Methyl (S)-3-amino-2-diethylaminopropanoate hydrochloride

In a manner similar to Example 2-3, starting from 189 mg (0.7 mmol) of methyl (S)-3-tert-butoxycarbonylamino-2-diethylaminopropanoate, 283 mg (quantitative yield) of methyl (S)-3-amino-2-diethylaminopropanoate hydrochloride are obtained in the form of a white solid.

11-4: Methyl (S)-2-diethylamino-3-[4-(2-methoxyethoxymethoxy)benzoylamino]propanoate In a manner similar to Example 4-3, starting from 283 mg (0.7 mmol) of methyl (S)-3-amino-2-diethylaminopropanoate hydrochloride and from 156 mg (0.7 mmol) of 4-(2-methoxyethoxymethoxy)benzoic acid (prepared as described in 4-2), 136 mg (52%) of methyl (S)-2-diethylamino-3-[4-(2-methoxyethoxymethoxy)benzoylamino]-propanoate are obtained in the form of a yellow oil.

11-5: Methyl (S)-2-diethylamino-3-(4-hydroxybenzoylamino)propanoate

In a manner similar to Example 4-4, starting from 136 mg (0.4 mmol) of methyl (S)-2-diethylamino-3-[4-(2-methoxyethoxymethoxy)benzoylamino]propanoate, 95 mg (90%) of methyl (S)-2-diethylamino-3-(4-hydroxybenzoyl-amino)propanoate are obtained in the form of a yellow oil.

11-6: Methyl (S)-2-diethylamino-3-[4-(2-methylquinolin-4-ylmethoxy)benzoylamino]propanoate In a manner similar to Example 19-1, starting from mg (0.3 mmol) of methyl (S)-2-diethylamino-3-(4-hydroxy-benzoylamino)propanoate and from 68 mg (0.4 mmol) of 4-chloromethyl-2-methylquinoline, 90 mg (62%) of methyl (S)-2-diethylamino-3-[4-(2-methyl-quinolin-4-ylmethoxy)benzoylamino]propanoate are obtained in the form of an orange solid.

11-7: (S)-2-diethylamino-3-[4-(2-methylquinolin-4-ylmethoxy)benzoylamino]propanoic acid In a manner similar to Example 2-5, starting from 90 mg (0.2 mmol) of methyl (S)-2-diethylamino-3-[4-(2-methylquinolin-4-ylmethoxy)benzoylamino]propanoate, 97 mg (100%) of (S)-2-diethylamino-3-[4-(2-methylquinolin-4-ylmethoxy)benzoylamino]propanoic acid are obtained in the form of a light-orange solid.

11-8: N—((S)-2-diethylamino-2-hydroxycarbamoylethyl)-4-(2-methylquinolin-4-ylmethoxy)benzamide In a manner similar to Example 27-3, starting from 97 mg (0.2 mmol) of (S)-2-diethylamino-3-[4-(2-methylquinolin-4-ylmethoxy)benzoylamino]propanoic acid, 75 mg (75%) of N—((S)-2-diethylamino-2-hydroxycarbamoylethyl)-4-(2-methylquinolin-4-ylmethoxy)benzamide are obtained in the form of a beige powder.

$^1$H NMR (δ, DMSO): 0.96 (t, J=7.2 Hz, 6H); 2.47 (m, 2H); 2.67 (s, 3H); 2.71 (m, 2H); 3.41 (m, 2H); 3.49 (m, 1H); 5.68 (s, 2H); 7.21 (d, J=8.8 Hz, 2H); 7.58 (m, 2H); 7.75 (t, J=6.7 Hz, 1H); 7.84 (d, J=8.7 Hz, 2H); 7.97 (d, J=8.5 Hz, 1H); 8.12 (d, J=8.3 Hz, 1H); 8.21 (m, 1H); 8.80 (m, 1H); 10.45 (m, 1H).

Example 12

Enzymatic Test of TACE Inhibition

Description of the Test

The products are dissolved so as to obtain a concentration of 10 mM in DMSO. A 3-fold serial dilution is carried out over 10 steps so as to have a concentration range going from 10 µM to a final concentration of 0.5 nM.

The TACE enzyme is an internal production (carried out according to the publication "Protein Eng Des Sel, 2006, 19, 155-161") and is added so as to have a signal equivalent to 6 times the background noise over 2 h at 37° C. The reaction takes place in a buffered medium: Tris 50 mM, 4% of glycerol, pH 7.4. The fluorescent substrate is MCA-Pro-Leu-Ala-Val-(Dpa)-Arg-Ser-Ser-Arg-NH2 (R&D system reference: ES003). The substrate is cleaved by the enzyme between alanine and valine thus releasing a fluorescent peptide (excitation: 320 nm, emission: 420 nm). The substrate is used at 40 µM. The reaction is carried out in a final volume of 10 µl (4 µl inhibitor, 4 µl substrate, 2 µl enzyme) in a plate of 384 low-volume wells (Corning reference: 3676). The plate is incubated for 2 h at ambient temperature, then read in fluorescence mode using a Pherastar (BMG labtech). The $IC_{50}$ values are determined using mathematical processing software (XLfit).

Test of the Products

| Example No. | % TACE inhibition at 10 µM | $IC_{50}$ - TACE (nM) |
| --- | --- | --- |
| Ex1 | 96 | 9 |
| Ex2 | 100 | 71 |
| Ex3 | 97 | 255 |
| Ex4 | 100 | 61 |
| Ex5 | 93 | 108 |
| Ex6 | 93 | 70 |
| Ex7 | 90 | 91 |
| Ex8 | 91 | 105 |
| Ex9 | 92 | 428 |
| Ex10 | 90 | 900 |
| Ex11 | 91 | 232 |

On the basis of the results obtained in the enzymatic TACE test described above, the compounds claimed in the present invention are TNF-alpha converting enzyme (TACE) inhibitors and therefore may be potential active principles for the treatment of pathologies for which reducing TNF-alpha production would be of great benefit.

Example 13

Selectivity Test

Test Principle

The molecules are tested in dose-response studies on the following enzymes MMP1, MMP3, MMP9, ADAM9 and ADAM10 according to the same protocol as that described for the TACE enzyme in example 28 but with different substrates (MMP R&D system reference: P126-990 and ADAM R&D system reference: ES003).
The enzymes are purchased from Calbiochem.
Test of the Products

| | $IC_{50}$ (nM) | | | | | |
|---|---|---|---|---|---|---|
| Example | MMP1 | MMP3 | MMP9 | ADAM9 | ADAM10 | TACE |
| 2 | 9946 | >10000 | >10000 | >10000 | 6405 | 71 |
| 4 | >10000 | >10000 | >10000 | >10000 | >10000 | 61 |
| 5 | >10000 | 6125 | >10000 | >10000 | 3091 | 108 |
| 11 | >10000 | >10000 | >10000 | >10000 | >10000 | 232 |
| Apratastat | 145 | 10 | 82 | 85 | 71 | 5 |

On the basis of the results obtained in the selectivity test described above, these compounds are also highly selective for TACE compared to other ADAMs and MMPs, that is to say that they have $IC_{50}$ values for other ADAMs or MMPs at least 10 times greater than that obtained for TACE, and more advantageously at least 100 times greater.
The selective inhibition of TACE compared to these other enzymes should make it possible to reduce undesirable side effects during the administration of these molecules for the treatment of pathologies for which reducing TNF-alpha production would be of great benefit.

The invention claimed is:
1. A compound of formula (I) below:

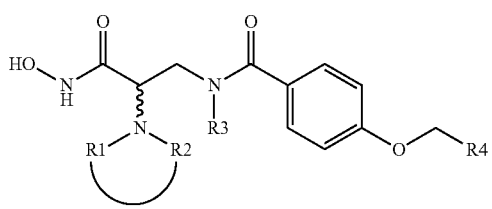

(I)

in which:
R₁ and R₂ are identical or different and represent alkyl radicals or else they form a ring with the nitrogen atom to which they are attached, said ring has the following formula:

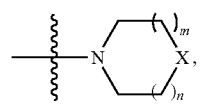

R₃ is a hydrogen atom or a lower alkyl radical comprising from 1 to 4 carbon atoms;

R₄ is an alkyl radical comprising from 1 to 10 carbon atoms; an alkyl radical substituted with one or more radicals selected from the group consisting of a halogen, an alkoxy radical, and a hydroxyl radical; an alkenyl radical comprising from 2 to 10 carbon atoms; an alkenyl radical substituted with one or more radicals selected from the group consisting of a halogen, an alkoxy radical and a hydroxyl radical; an alkynyl radical comprising from 2 to 10 carbon atoms; an alkynyl radical substituted with one or more radicals selected from the group consisting of a halogen, an alkoxy radical, and a hydroxyl radical; an aryl radical; an aryl radical substituted with one or more radicals selected from the group consisting of an alkyl, an alkoxy, an aryl, a halogen, a hydroxyl, a cyano, a trifluoromethyl, and a nitro; an aralkyl radical; a substituted aralkyl radical; a heterocyclic radical; a heterocyclic radical substituted with one or more radicals selected from the group consisting of an alkyl, an alkoxy, a halogen, a hydroxyl, a cyano, a trifluoromethyl, and a nitro; a cycloalkyl radical; a cycloalkyl radical substituted with one or more radicals selected from the group consisting of a halogen, an alkoxy radical, and a hydroxyl radical; a heteroaralkyl radical; or a heteroaralkyl radical substituted with one or more radicals selected from the group consisting of an alkyl, an alkoxy, a halogen, a hydroxyl, a cyano, a trifluoromethyl, and a nitro;
X represents an oxygen atom; a —CH₂— radical; a —CH—(CH₂)ₚ—NR₅R₆ radical; a sulphur atom; an SO radical; or an SO₂ radical;
R₅ and R₆, which may be identical or different, represent a hydrogen atom; an alkyl radical comprising from 1 to 10 carbon atoms; an alkyl radical substituted with one or more radicals selected from the group consisting of a halogen, an alkoxy radical, and a hydroxyl radical; an aryl radical; or an aryl radical substituted with one or more radicals selected from the group consisting of an alkyl, an alkoxy, an aryl, a halogen, a hydroxyl, a cyano, a trifluoromethyl, and a nitro;
m takes the values of 0 or 1;
n takes the values of 0, 1, 2, or 3; and
p takes the values of 0, 1, or 2;
and also an addition salt of the compound of formula (I) with a pharmaceutically acceptable acid; an addition salt of the compound of formula (I) with a pharmaceutically acceptable base; or an enantiomer of the compound of formula (I).
2. The addition salt of the compound according to claim 1 with a pharmaceutically acceptable acid, wherein the pharmaceutically acceptable acid is selected from the group consisting of hydrochloric acid, hydrobromic acid, sulphuric acid, nitric acid, phosphoric acid, acetic acid, trifluoroacetic acid, trichloroacetic acid, propionic acid, glycolic acid, pyruvic acid, succinic acid, benzoic acid, cinnamic acid, mandelic acid, methanesulphonic acid, para-toluenesulphonic acid, salicylic acid, picric acid, citric acid, oxalic acid, tartaric acid, malonic acid, maleic acid, camphorsulphonic acid, and fumaric acid.
3. The addition salt of the compound according to claim 1 with a pharmaceutically acceptable base, wherein the pharmaceutically acceptable base is selected from the group consisting of potassium hydroxide, sodium hydroxide, lithium hydroxide, calcium hydroxide, sodium carbonate, potassium carbonate, calcium carbonate, methylamine, ethylamine, ethanolamine, propylamine, isopropylamine, the 4 isomers of butylamine, dimethylamine, diethylamine, diethanolamine, dipropylamine, diisopropylamine, di-n-butylamine, pyrrolidine, piperidine, morpholine, diethanolphenylamine, trimethylamine, triethylamine, tripropylamine, quinuclidine, pyridine, quinoline, isoquinoline, lysine, arginine, and ornithine.

4. The compound according to claim 1, wherein:

$R_1$ and $R_2$, which are identical or different, represent alkyl radicals or else they form a ring with the nitrogen atom to which they are attached, said ring has the following formula:

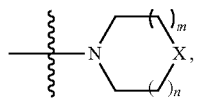

$R_3$ is a hydrogen atom or a lower alkyl radical;
$R_4$ is an alkynyl radical; a substituted alkynyl radical; an aryl radical; a substituted aryl radical; an aralkyl radical; a substituted aralkyl radical; a heterocyclic radical; a substituted heterocyclic radical; a heteroaralkyl radical; or a substituted heteroaralkyl radical;
X represents an oxygen atom; a —$CH_2$— radical; a —CH—$(CH_2)_p$—$NR_5R_6$ radical; a sulphur atom; an SO radical; or an $SO_2$ radical;
$R_5$ and $R_6$, which may be identical or different, represent a hydrogen atom; an alkyl radical; a substituted alkyl radical; an aryl radical; or a substituted aryl radical;
m takes the values of 0 or 1;
n takes the values of 0, 1, or 2; and
p takes the values of 0, 1, or 2;
and also an addition salt of the compound of formula (I) with a pharmaceutically acceptable acid; an addition salt of the compound of formula (I) with a pharmaceutically acceptable base; or an enantiomer of the compound of formula (I).

5. The compound according to claim 1, wherein:

$R_1$ and $R_2$ are identical or different and represent alkyl radicals or else they form a ring with the nitrogen atom to which they are attached, said ring has the following formula:

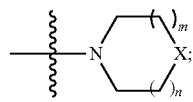

$R_3$ is a hydrogen atom or a lower alkyl radical;
$R_4$ is an alkynyl radical; a substituted alkynyl radical; an aryl radical; a substituted aryl radical; an aralkyl radical; a substituted aralkyl radical; a heterocyclic radical; a substituted heterocyclic radical; a heteroaralkyl radical; or a substituted heteroaralkyl radical;
X represents an oxygen atom; a —$CH_2$— radical; or a —CH—$(CH_2)_p$—$NR_5R_6$ radical;
$R_5$ and $R_6$, which may be identical or different, represent a hydrogen atom; an alkyl radical; a substituted alkyl radical; an aryl radical; or a substituted aryl radical;
m takes the value of 1;
n takes the values of 0, 1, or 2; and
p takes the values of 0, 1, or 2;
and also an addition salt of the compound of formula (I) with a pharmaceutically acceptable acid; an addition salt of the compound of formula (I) with a pharmaceutically acceptable base; or an enantiomer of the compound of formula (I).

6. The compound according to claim 1, wherein:

$R_1$ and $R_2$ form a ring with the nitrogen atom to which they are attached, said ring has the following formula:

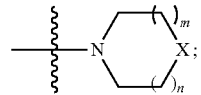

$R_3$ is a hydrogen atom;
$R_4$ is an aryl radical; a substituted aryl radical; an aralkyl radical; a substituted aralkyl radical; a heterocyclic radical; a substituted heterocyclic radical; a heteroaralkyl radical; or a substituted heteroaralkyl radical;
X represents an oxygen atom; a —$CH_2$— radical; or a —CH—$(CH_2)_p$—$NR_5R_6$ radical;
$R_5$ and $R_6$, which may be identical or different, represent a hydrogen atom; an alkyl radical; a substituted alkyl radical; an aryl radical; or a substituted aryl radical;
m takes the value of 1;
n takes the values of 1 or 2; and
p takes the values of 0, 1, or 2;
and also an addition salt of the compound with a pharmaceutically acceptable acid; an addition salt of the compound with a pharmaceutically acceptable base; or an enantiomer of the compound of formula (I).

7. The compound according to claim 1, wherein:

$R_1$ and $R_2$ form a ring with the nitrogen atom to which they are attached, said ring has the following formula:

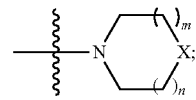

$R_3$ is a hydrogen atom;
$R_4$ is a heterocyclic radical; a substituted heterocyclic radical; a heteroaralkyl radical; or a substituted heteroaralkyl radical;
X represents an oxygen atom or a —$CH_2$— radical;
m takes the value of 1; and
n takes the value of 1;
and also an addition salt of the compound of formula (I) with a pharmaceutically acceptable acid; an addition salt of the compound of formula (I) with a pharmaceutically acceptable base; or an enantiomer of the compound.

8. The compound according to claim 1, wherein:

$R_1$ and $R_2$ form a ring with the nitrogen atom to which they are attached, said ring has the following formula:

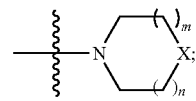

$R_3$ is a hydrogen atom;
$R_4$ is a heteroaryl radical or a substituted heteroaryl radical;
X represents an oxygen atom or a —$CH_2$— radical;
m takes the value of 1; and
n takes the value of 1;
and also an addition salt of the compound of formula (I) with a pharmaceutically acceptable acid; an addition salt of the compound of formula (I) with a pharmaceutically acceptable base; or an enantiomer of the compound of formula (I).

9. A compound selected from the group consisting of:
4-but-2-ynyloxy-N—((S)-2-hydroxycarbamoyl-2-piperidin-1-ylethyl)benzamide;
N—((S)-2-hydroxycarbamoyl-2-piperidin-1-ylethyl)-4-(2-methyl-quinolin-4-ylmethoxy)-benzamide;
N—((S)-2-hydroxycarbamoyl-2-piperidin-1-ylethyl)-4-(2-phenyl-pyridin-4-ylmethoxy)-benzamide;
N—((S)-2-hydroxycarbamoyl-2-piperidin-1-ylethyl)-4-(pyridin-4-ylmethoxy)-benzamide;
4-(4-cyanobenzyloxy)-N—((S)-2-hydroxycarbamoyl-2-piperidin-1-yl-ethyl)-benzamide;
N—((S)-2-hydroxycarbamoyl-2-piperidin-1-yl-ethyl)-4-(4-methyl-naphthalen-1-yl-methoxy)-benzamide;
4-(2-bromopyridin-4-ylmethoxy)-N—((S)-2-hydroxy-carbamoyl-2-piperidin-1-yl-ethyl)-benzamide;
N—((S)-2-hydroxycarbamoyl-2-morpholin-4-yl-ethyl)-4-(pyridin-4-yl-methoxy)-benzamide;
N—((S)-2-hydroxycarbamoyl-2-morpholin-4-yl-ethyl)-4-[2-(2-trifluoro-methyl-phenyl)-pyridin-4-yl-methoxy]-benzamide;
N—((S)-2-diethylamino-2-hydroxycarbamoyl-ethyl)-4-(2-methyl-quinolin-4-yl-methoxy)-benzamide;
N—((S)-2-hydroxycarbamoyl-2-pyrrolidin-1-yl-ethyl)-4-(2-methyl-quinolin-4-yl-methoxy)-benzamide;
N—((S)-2-hydroxycarbamoyl-2-pyrrolidin-1-yl-ethyl)-4-(3-methyl-benzyloxy)-benzamide;
N—((R)-2-hydroxycarbamoyl-2-piperidin-1-yl-ethyl)-4-(2-methyl-quinolin-4-yl-methoxy)-benzamide;
N—((R)-2-azepan-1-yl-2-hydroxycarbamoyl-ethyl)-4-(2-methyl-quinolin-4-yl-methoxy)-benzamide;
N—((S)-2-azepan-1-yl-2-hydroxycarbamoyl-ethyl)-4-(2-methyl-quinolin-4-yl-methoxy)-benzamide;
N—((S)-2-hydroxycarbamoyl-2-[1,4]oxazepan-4-yl-ethyl)-4-(2-methyl-pyridin-4-yl-methoxy)-benzamide;
N—((S)-2-hydroxycarbamoyl-2-thiomorpholin-4-yl-ethyl)-4-(1-methylpiperidin-4-yl-methoxy)-benzamide;
N—((S)-2-hydroxycarbamoyl-2-thiomorpholin-4-yl-ethyl)-4-(2-methyl-quinolin-4-yl-methoxy)-benzamide;
N—((S)-2-hydroxycarbamoyl-2-piperidin-1-yl-ethyl)-4-(pyrazolo-[1,5-a]-pyridin-3-yl-methoxy)-benzamide;
N—((S)-2-hydroxycarbamoyl-2-morpholin-4-O-ethyl)-4-(2-trifluoro-methyl-pyrazolo[1,5-a]-pyridin-3-yl-methoxy)-benzamide;
N—((S)-2-hydroxycarbamoyl-2-piperidin-1-ylethyl)-4-(2-trifluoro-methyl-pyrazolo[1,5-a]-pyridin-3-yl-methoxy)-benzamide;
N—[(S)-2-(1,1-dioxothiomorpholin-4-yl)-2-hydroxy-carbamoyl-ethyl]-4-(4-fluoro-benzyloxy)-benzamide;
N—((S)-2-hydroxycarbamoyl-2-pyrrolidin-1-yl-ethyl)-4-(2-methyl-naphthalen-1-yl-methoxy)-N-propyl-benzamide;
N—((S)-2-hydroxycarbamoyl-2-pyrrolidin-1-yl-ethyl)-4-propoxy-benzamide;
N—((S)-2-hydroxycarbamoyl-2-piperidin-1-yl-ethyl)-4-(quinolin-4-yl-methoxy)-benzamide;
N—((S)-2-azocan-1-yl-2-hydroxycarbamoyl-ethyl)-4-(3-methyl-1H-pyrazol-4-yl-methoxy)-benzamide;
4-(3,5-dimethylbenzyloxy)-N—((S)-2-hydroxy-carbamoyl-2-[1,4]oxazocan-4-ylethyl)-benzamide;
4-(2,6-dimethylpyridin-4-yl-methoxy)-N—[(S)-2-(ethyl-propyl-amino)-2-hydroxy-carbamoyl-ethyl]-benzamide;
N—((R)-2-azepan-1-yl-2-hydroxy-cabamoyl-ethyl)-4-(2-methyl-pyridin-4-yl-methoxy)-benzamide;
N—[(S)-2-(4-ethylamino-piperidin-1-yl)-2-hydroxycarbamoyl-ethyl]-4-(2-methyl-quinolin-4-yl-methoxy)-benzamide;
N—[(S)-2-(3-amino-pyrrolidin-1-yl)-2-hydroxy-carbamoyl-ethyl]-4-(2-methyl-quinolin-4-yl-methoxy)-benzamide;
N—[(S)-2-(3-dimethylaminomethyl-pyrrolidin-1-yl)-2-hydroxy-carbamoyl-ethyl]-4-(2-methyl-quinolin-4-yl-methoxy)-benzamide;
N—[(S)-2-(4-benzylaminopiperidin-1-yl)-2-hydroxy-carbamoyl-ethyl]-4-(2-methyl-pyridin-4-yl-methoxy)-benzamide; and
N—[(S)-2-(4-dimethylaminomethyl-azepan-1-yl)-2-hydroxy-carbamoyl-ethyl]-4-(2-methyl-1H-indol-3-yl-methoxy)-benzamide;
and also addition salts of the compound with a pharmaceutically acceptable acid and addition salts of the compound with a pharmaceutically acceptable base.

10. A pharmaceutical composition comprising the compound according to claim 1, an addition salt thereof, or an enantiomer thereof.

11. The compound according to claim 1, wherein the heterocyclic radical is a heteroaryl radical.

12. The compound according to claim 1, wherein the substituted heterocyclic radical is a heteroaryl radical substituted with one or more radicals selected from the group consisting of an alkyl, an alkoxy, an aryl, a substituted aryl, a halogen, a hydroxyl, a cyano, a trifluoromethyl, and a nitro.

13. The compound according to claim 4, wherein the heterocyclic radical is a heteroaryl radical.

14. The compound according to claim 4, wherein the substituted heterocyclic radical is a heteroaryl radical substituted with one or more radicals selected from the group consisting of an alkyl, an alkoxy, an aryl, a substituted aryl, a halogen, a hydroxyl, a cyano, a trifluoromethyl, and a nitro.

15. The compound according to claim 5, wherein the heterocyclic radical is a heteroaryl radical.

16. The compound according to claim 5, wherein the substituted heterocyclic radical is a heteroaryl radical substituted with one or more radicals selected from the group consisting of an alkyl, an alkoxy, an aryl, a substituted aryl, a halogen, a hydroxyl, a cyano, a trifluoromethyl, and a nitro.

17. The compound according to claim 6, wherein the heterocyclic radical is a heteroaryl radical.

18. The compound according to claim 6, wherein the substituted heterocyclic radical is a heteroaryl radical substituted with one or more radicals selected from the group consisting of an alkyl, an alkoxy, an aryl, a substituted aryl, a halogen, a hydroxyl, a cyano, a trifluoromethyl, and a nitro.

19. The compound according to claim 7, wherein the heterocyclic radical is a heteroaryl radical.

20. The compound according to claim 7, wherein the substituted heterocyclic radical is a heteroaryl radical substituted with one or more radicals selected from the group consisting of an alkyl, an alkoxy, an aryl, a substituted aryl, a halogen, a hydroxyl, a cyano, a trifluoromethyl, and a nitro.

* * * * *

UNITED STATES PATENT AND TRADEMARK OFFICE
CERTIFICATE OF CORRECTION

PATENT NO. : 9,266,848 B2
APPLICATION NO. : 13/496577
DATED : February 23, 2016
INVENTOR(S) : Laurence Clary et al.

Page 1 of 1

It is certified that error appears in the above-identified patent and that said Letters Patent is hereby corrected as shown below:

On the Title page, the Related U.S. Application Data section is incomplete:

It should read:
--Related U.S. Application Data

(60) Provisional application No. 61/272,368, filed on September 17, 2009--

Signed and Sealed this
Tenth Day of May, 2016

Michelle K. Lee
*Director of the United States Patent and Trademark Office*